US011548864B1

(12) United States Patent
Milani et al.

(10) Patent No.: US 11,548,864 B1
(45) Date of Patent: Jan. 10, 2023

(54) SEPARATION OF CHEMICAL SPECIES USING MULTIPLE LIQUID PHASES AND RELATED SYSTEMS

(71) Applicant: Zaiput Flow Technologies LLC, Waltham, MA (US)

(72) Inventors: Lorenzo Milani, Woburn, MA (US); Trevor Charles Murray, Everett, MA (US); Robert Viano, Medford, MA (US); Andrea Adamo, Cambridge, MA (US)

(73) Assignee: Zaiput Flow Technologies LLC, Waltham, MA (US)

( * ) Notice: Subject to any disclaimer, the term of this patent is extended or adjusted under 35 U.S.C. 154(b) by 0 days.

(21) Appl. No.: 17/840,914

(22) Filed: Jun. 15, 2022

(51) Int. Cl.
*C07D 311/78* (2006.01)

(52) U.S. Cl.
CPC .................. *C07D 311/78* (2013.01)

(58) Field of Classification Search
CPC .................................................. C07D 311/78
See application file for complete search history.

(56) References Cited

U.S. PATENT DOCUMENTS

| | | | |
|---|---|---|---|
| 706,812 | A | 8/1902 | Fenn |
| 2,985,589 | A | 5/1961 | Broughton et al. |
| 3,696,107 | A | 10/1972 | Neuzil |
| 3,706,812 | A | 12/1972 | Derosset et al. |
| 3,761,533 | A | 9/1973 | Otani et al. |
| 5,093,004 | A | 3/1992 | Hotier et al. |
| 5,114,590 | A | 5/1992 | Hotier et al. |
| 7,422,685 | B2 | 9/2008 | Couillard et al. |
| 9,321,715 | B2 | 4/2016 | Kelliher et al. |
| 10,501,432 | B2 * | 12/2019 | Runco ............... B01J 20/3231 |
| 10,624,872 | B1 * | 4/2020 | McCorkle ............ C07C 37/84 |
| 10,941,131 | B1 * | 3/2021 | Grondin ............ C07D 311/80 |
| 2018/0036278 | A1 | 2/2018 | Rutz |

FOREIGN PATENT DOCUMENTS

| | | |
|---|---|---|
| CN | 101732890 B | 1/2012 |
| FR | 2103302 A5 | 4/1972 |
| FR | 2651148 A1 | 3/1991 |
| FR | 2651149 A1 | 3/1991 |
| JP | 2019-108340 A | 7/2019 |
| WO | WO 2005/011835 A1 | 2/2005 |
| WO | WO 2010/010366 A1 | 1/2010 |

OTHER PUBLICATIONS

[No Author Listed], Introduction to Continuous (SMB) Chromatography. Jul. 16, 2014. https://sembabio.com/simulated-moving-bed-chromatography/ [last accessed Jun. 21, 2022]. 4 pages.
Adelmann et al., Influence of physical properties and operating parameters on hydrodynamics in Centrifugal Partition Chromatography. J Chromatogr A. Aug. 12, 2011;1218(32):5401-13. doi: 10.1016/j.chroma.2011.01.064. Epub Jan. 27, 2011.
Berthod et al., Countercurrent chromatography: people and applications. J Chromatogr A. May 8, 2009;1216(19):4206-17. doi: 10.1016/j.chroma.2008.10.071. Epub Oct. 22, 2008.
Chen et al., Preparative isolation and purification of cuminaldehyde and p-menta-1,4-dien-7-al from the essential oil of *Cuminum cyminum* L. by high-speed counter-current chromatography. Anal Chim Acta. Mar. 9, 2011;689(1):149-54. doi: 10.1016/j.aca.2011.01.038. Epub Jan. 25, 2011.
Choi et al., NMR assignments of the major cannabinoids and cannabiflavonoids isolated from flowers of *Cannabis sativa*. Phytochem Anal. Nov.-Dec. 2004;15(6):345-54. doi: 10.1002/pca.787.
Foucault, Solvent Systems in Centrifugal Partition Chromatography. Chromatographic Science Series. 1994. Foucault, Ed. Chapter 4:71-97.
Foucault, Theory of Centrifugal Partition Chromatography. In: Centrifugal Partition Chromatography. Chromatographic Science Series. 1994. Foucault, Ed. Chapter 2:25-49.
Friesen et al., Countercurrent Separation of Natural Products: An Update. J Nat Prod. Jul. 24, 2015;78(7):1765-96. doi: 10.1021/np501065h. Epub Jul. 15, 2015.
Ganetsos et al., Preparative and Production Scale Chromatography. 1993. Ganetsos et al., Eds. 372 pages.
Gomes et al., Simulated Moving Bed Chromatography: From Concept to Proof-of-Concept. Chem Eng Tech. Dec. 2, 2011;35(1):17-34.
Han et al., Preparative separation of gambogic acid and its C-2 epimer using recycling high-speed counter-current chromatography. J Chromatogr A. Sep. 15, 2006;1127(1-2):298-301. doi: 10.1016/j.chroma.2006.07.044. Epub Aug. 2, 2006.
Hazekamp et al., Chromatographic and Spectroscopic Data of Cannabinoids from *Cannabis sativa* L.. J Liquid Chromatogr Rel Tech. 2005;28(15):2361-82.
Hazekamp et al., Preparative Isolation of Cannabinoids from Cannabis sativa by Centrifugal Partition Chromatography. J Liquid Chromatogr Rel Tech. Apr. 2004;27(15):2421-39.
Hazekamp, Cannabis: extracting the medicine. Doctoral Thesis. Leiden University. Sep. 5, 2007:190 pages.
Ito, Golden rules and pitfalls in selecting optimum conditions for high-speed counter-current chromatography. J Chromatogr A. Feb. 18, 2005;1065(2):145-68. doi: 10.1016/j.chroma.2004.12.044.
Lorantfy et al., Continuous Industrial-Scale Centrifugal Partition Chromatography with Automatic Solvent System Handling: Concept and Instrumentation. Org Process Res Dev. Nov. 6, 2020;24(11):2676-88.
Margraff, Preparative Centrifugal Partition Chromatography. Chromatographic Science Series. 1994. Foucault, Ed. Chapter 12:331-350.
Orkenyi et al., Continuous Synthesis and Purification by Coupling a Multistep Flow Reaction with Centrifugal Partition Chromatography. Angew Chem Int Ed Engl. Jul. 17, 2017;56(30):8742-8745. doi: 10.1002/anie.201703852. Epub Jun. 19, 2017.
Queiroga et al., High-speed countercurrent chromatography as a tool to isolate nerolidol from the Baccharis dracunculifolia volatile oil. J Ess Oil Res. May 2014;26(5):334-37.
Strube et al., Comparison of Batch Elution and Continuous Simulated Moving Bed Chromatography. Org Proc Res Dev. Jul. 18, 1998;2(5):305-19.

(Continued)

*Primary Examiner* — Golam M Shameem
(74) *Attorney, Agent, or Firm* — Wolf, Greenfield & Sacks, P.C.

(57) ABSTRACT

The present disclosure is related to the separation of chemical species using multiple liquid phases.

30 Claims, 3 Drawing Sheets

(56) References Cited

OTHER PUBLICATIONS

Wang et al., Bioassay-guided isolation of an active compound with protein tyrosine phosphatase 1B inhibitory activity from Sargassum fusiforme by high-speed counter-current chromatography. J Sep Sci. Nov. 2016;39(22):4408-4414. doi: 10.1002/jssc.201600691. Epub Oct. 24, 2016.

Weeranoppanant et al., Design of Multistage Counter-Current Liquid-Liquid Extraction for Small-Scale Applications. Ind Eng Chem Res. Mar. 22, 2017;56(14):4095-103.

Xie et al., Isolation and purification of nootkatone from the essential oil of fruits of Alpinia oxyphylla Miquel by high-speed counter-current chromatography. Food Chem. Nov. 2009;117(2):375-380. doi: 10.1016/j.foodchem.2009.04.011.

\* cited by examiner

SEPARATION OF CHEMICAL SPECIES USING MULTIPLE LIQUID PHASES AND RELATED SYSTEMS

TECHNICAL FIELD

Separation of chemical species using multiple liquid phases and related systems are generally described.

SUMMARY

The present disclosure is related to the separation of chemical species using multiple liquid phases. Related systems and articles are also described. The subject matter of the present invention involves, in some cases, interrelated products, alternative solutions to a particular problem, and/or a plurality of different uses of one or more systems and/or articles.

In certain aspects, methods of separating delta-9-tetrahydrocannabinol from delta-8-tetrahydrocannabinol are provided. In some embodiments, the method comprises exposing a mixture comprising the delta-9-tetrahydrocannabinol and the delta-8-tetrahydrocannabinol to a heterogeneous liquid mixture, wherein the heterogeneous liquid mixture comprises a first liquid phase and a second liquid phase, wherein: the mole fraction of the delta-9-tetrahydrocannabinol relative to the sum of the delta-9-tetrahydrocannabinol and the delta-8-tetrahydrocannabinol in the first liquid phase is greater than the mole fraction of the delta-9-tetrahydrocannabinol relative to the sum of the delta-9-tetrahydrocannabinol and the delta-8-tetrahydrocannabinol in the mixture; and the mole fraction of the delta-8-tetrahydrocannabinol relative to the sum of the delta-8-tetrahydrocannabinol and the delta-9-tetrahydrocannabinol in the second liquid phase is greater than the mole fraction of the delta-8-tetrahydrocannabinol relative to the sum of the delta-8-tetrahydrocannabinol and the delta-9-tetrahydrocannabinol in the mixture.

In some embodiments, the method comprises exposing a mixture comprising the delta-9-tetrahydrocannabinol and the delta-8-tetrahydrocannabinol to a heterogeneous liquid mixture, wherein the heterogeneous liquid mixture comprises a first liquid phase and a second liquid phase, such that the delta-9-tetrahydrocannabinol preferentially associates with the first liquid phase and the delta-8-tetrahydrocannabinol preferentially associates with the second liquid phase.

In certain aspects, methods of separating delta-9-tetrahydrocannabinol from one or more additional cannabinoids are provided. In some embodiments, the method comprises exposing a mixture comprising the delta-9-tetrahydrocannabinol and the one or more additional cannabinoids to a heterogeneous liquid mixture, wherein the heterogeneous liquid mixture comprises a first liquid phase and a second liquid phase, wherein: the mole fraction of the delta-9-tetrahydrocannabinol relative to the sum of the delta-9-tetrahydrocannabinol and the one or more additional cannabinoids in the first liquid phase is greater than the mole fraction of the delta-9-tetrahydrocannabinol relative to the sum of the delta-9-tetrahydrocannabinol and the one or more additional cannabinoids in the mixture; and the mole fraction of the one or more additional cannabinoids relative to the sum of the one or more additional cannabinoids and the delta-9-tetrahydrocannabinol in the second liquid phase is greater than the mole fraction of the one or more additional cannabinoids relative to the sum of the one or more additional cannabinoids and the delta-9-tetrahydrocannabinol in the mixture.

In some embodiments, the method comprises exposing a mixture comprising the delta-9-tetrahydrocannabinol and the one or more additional cannabinoids to a heterogeneous liquid mixture, wherein the heterogeneous liquid mixture comprises a first liquid phase and a second liquid phase, such that the delta-9-tetrahydrocannabinol preferentially associates with the first liquid phase and the one or more additional cannabinoids preferentially associates with the second liquid phase.

Certain aspects are related to ingestible compositions. In some embodiments, the ingestible composition comprises delta-9-tetrahydrocannabinol and delta-8-tetrahydrocannabinol, wherein: the ingestible composition has a volume of at least 1 mm$^3$; a molar ratio of delta-9-tetrahydrocannabinol to delta-8-tetrahydrocannabinol within the ingestible composition is greater than or equal to 3:1; and the amount of delta-9-tetrahydrocannabinol within the ingestible composition is at least 0.01 wt %.

In some embodiments, the ingestible composition comprises delta-9-tetrahydrocannabinol and one or more additional cannabinoids, wherein: the ingestible composition has a volume of at least 1 mm$^3$; a molar ratio of delta-9-tetrahydrocannabinol to the one or more additional cannabinoids of greater than or equal to 3:1; and delta-9-tetrahydrocannabinol within the ingestible composition is at least 0.01 wt %.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale unless otherwise indicated. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
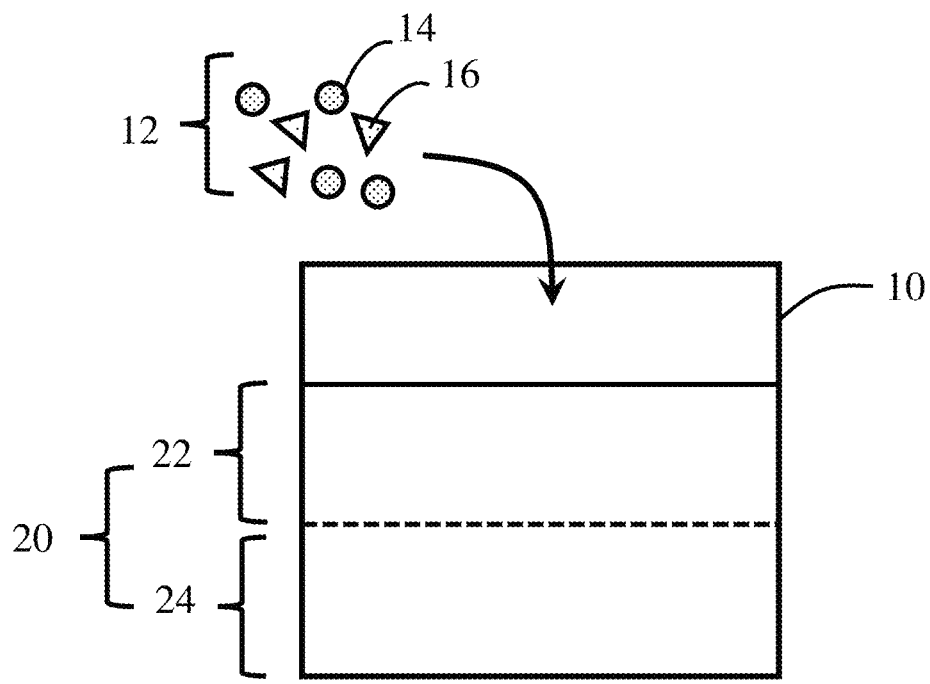
FIGS. 1A-1D are schematic illustrations showing a method for separating delta-9-tetrahydrocannabinol from one or more cannabinoids, according to some embodiments.

Separation of chemical species using multiple liquid phases and related systems are generally described. Certain aspects of the present disclosure are directed to the discovery that the use of certain heterogeneous liquid mixtures can allow for highly specific and targeted separation of a specific cannabinoid (e.g., delta-9-tetrahydrocannabinol) from one or more additional cannabinoids in a mixture. Certain embodiments are related to the discovery that the use of a heterogeneous liquid mixture comprising a first liquid phase, e.g., such as a liquid comprising an amide group, and a second liquid phase immiscible with the first liquid phase, e.g., such as a non-polar hydrocarbon, can provide, in certain instances, one or more of a variety of operational advantages. Such operational advantages include, but are not limited to, a continuous extraction process, a high extraction efficiency associated with a specific cannabinoid, reduced amount of extraction liquid and/or reduced number of extraction stages associated with the separation process. Some embodiments are related to the discovery that effective separation of a specific cannabinoid (e.g., delta-9-tetrahydrocannabinol) can be achieved by using liquids that provide different partition coefficients of the specific cannabinoid and the one or more additional cannabinoids in the heterogeneous liquid mixture. It has also been recognized, within the context of the present disclosure, that the methods described herein can be advantageously employed in the purification of cannabinoid oils obtained from raw biomass. Compared to conventional methods, the methods described herein can allow one to target a specific cannabinoid (e.g., delta-9-tetrahydrocannabinol), use less solvent(s), and/or reduce overall operational costs associated with the separation process.

In some embodiments, a method for separating delta-9-tetrahydrocannabinol from one or more additional cannabinoids is described. The method, according to some embodiments, may be employed for separating delta-9-tetrahydrocannabinol from any of a variety of cannabinoids. For example, in one set of embodiments, the method may be employed for separating delta-9-tetrahydrocannabinol from delta-8-tetrahydrocannabinol, a constitutional (e.g., structural) isomer of delta-9-tetrahydrocannabinol. Alternatively or additionally, the method may be employed for separating delta-9-tetrahydrocannabinol from another cannabinoid, such as cannabidiol (CBD). Alternatively or additionally, the method may be employed for separating delta-9-tetrahydrocannabinol from a combination of various cannabinoids (e.g., delta-8-tetrahydrocannabinol, cannabidiol, etc.). Non-limiting examples of additional cannabinoids from which delta-9-tetrahydrocannabinol may be separated are described in more detail below.

FIGS. 1A-1D are schematic illustrations of one such non-limiting method that can be used to separate delta-9-tetrahydrocannabinol from one or more additional cannabinoids, according to some embodiments. These figures are referred to throughout the disclosure below.

The method, in some embodiments, comprises exposing a mixture comprising the delta-9-tetrahydrocannabinol and the one or more additional cannabinoids to a heterogeneous liquid mixture. The delta-9-tetrahydrocannabinol may have a chemical structure as shown in formula (I):

(I)

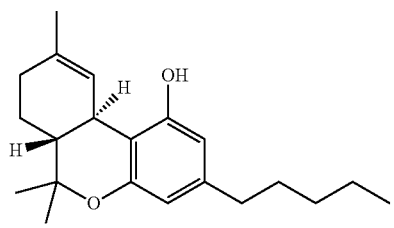

In some embodiments, the delta-9-tetrahydrocannabinol in the mixture may comprise one or more stereoisomers (i.e., spatial isomers) of delta-9-tetrahydrocannabinol. The one or more stereoisomers of delta-9-tetrahydrocannabinol may include conformational isomers of delta-9-tetrahydrocannabinol and/or configurational isomers of delta-9-tetrahydrocannabinol. The configurational isomers of delta-9-tetrahydrocannabinol may include enantiomers and/or diastereomers of delta-9-tetrahydrocannabinol. Non-limiting examples of delta-9-tetrahydrocannabinol include (−)-delta-9-trans-tetrahydrocannabinol (e.g., as shown in formula (II)), (+)-delta-9-trans-tetrahydrocannabinol (e.g., as shown in formula (III)), (−)-delta-9-cis-tetrahydrocannabinol (e.g., as shown in formula (IV)), and (+)-delta-9-cis-tetrahydrocannabinol (e.g., as shown in formula (V)).

(II)

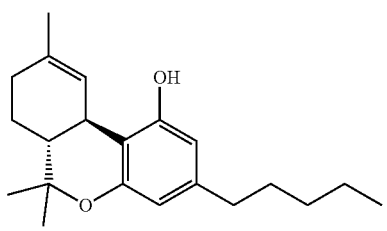

(III)

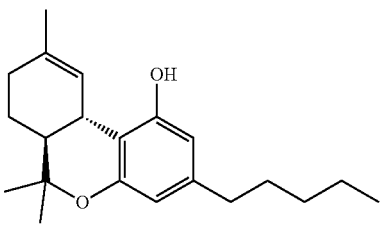

(IV)

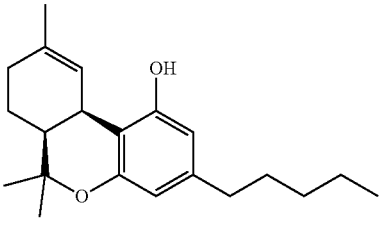

(V)

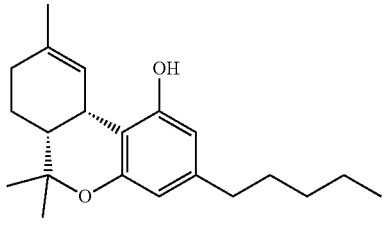

It should be noted that the delta-9-tetrahydrocannabinol described herein does not include constitutional (i.e., structural) isomers of delta-9-tetrahydrocannabinol. Non-limiting examples of constitutional (i.e., structural) isomers of delta-9-tetrahydrocannabinol include delta-8-tetrahydrocannabinol, delta-7-tetrahydrocannabinol, delta-10-tetrahydrocannabinol, delta-6a,7-tetrahydrocannabinol, delta-6a,10a-tetrahydrocannabinol, etc. It should also be noted that the delta-9-tetrahydrocannabinol described herein does not include acid forms of delta-9-tetrahydrocannabinol.

The mixture may include any of a variety of additional cannabinoids. Specific non-limiting examples of additional cannabinoids include delta-8-tetrahydrocannabinol (e.g., as shown in formula (VI)), cannabidiol (e.g., as shown in formula (VII)), other constitutional isomers of delta-9-tetrahydrocannabinol described herein, cannabigerol, cannabinol, and cannabichromene. In some embodiments, the delta- 8-tetrahydrocannabinol, a constitutional isomer of delta-9-tetrahydrocannabinol, may include one or more stereoisomers of delta-8-tetrahydrocannabinol. Non-limiting examples of delta-8-tetrahydrocannabinol include (−)-delta-8-trans-tetrahydrocannabinol, (+)-delta-8-trans-tetrahydrocannabinol, (−)-delta-8-cis-tetrahydrocannabinol, and/or (+)-delta-8-cis-tetrahydrocannabinol. The method described herein may be employed for separating delta-9-tetrahydrocannabinol from one or more of the additional cannabinoids described herein.

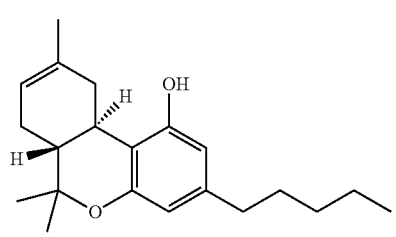

(VI)

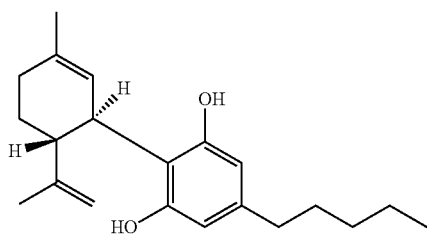

(VII)

The phrase "heterogeneous liquid mixture" is generally used herein to refer to a liquid mixture comprising two or more distinct liquid phases. The first liquid phase and the second liquid phase may be, in some embodiments, immiscible with each other. The two or more distinct liquid phases may, in some embodiments, have a low mutual solubility with each other. For example, in some embodiments, the two or more distinct liquid phases have a mutual solubility of less than or equal to 200 mg/mL, less than or equal to 100 mg/mL, less than or equal to 50 mg/mL, less than or equal to 10 mg/mL, less than or equal to 1 mg/mL, less than or equal to 0.1 mg/mL, less than or equal to 0.001 mg/mL, less than or equal to 0.0001 mg/mL, or less than or equal to 0.00001 mg/mL (and/or, as little as 0.00001 mg/mL, as little as 0.000001 mg/mL, or less) at the temperature at which the separation is carried out. In some embodiments, the two or more distinct liquid phases have a mutual solubility of less than or equal to 200 mg/mL, less than or equal to 100 mg/mL, less than or equal to 50 mg/mL, less than or equal to 10 mg/mL, less than or equal to 1 mg/mL, less than or equal to 0.1 mg/mL, less than or equal to 0.001 mg/mL, less than or equal to 0.0001 mg/mL, or less than or equal to 0.00001 mg/mL (and/or, as little as 0.00001 mg/mL, as little as 0.000001 mg/mL, or less) at 20° C. For example, in one set of embodiments, the heterogeneous liquid mixture may comprise a first liquid phase and a second liquid phase that is immiscible with the first liquid phase, e.g., such as polar liquid and a non-polar liquid. In some embodiments, the first liquid phase and the second liquid phase have mutual solubilities falling within any of the ranges outlined above.

FIG. 1A illustrates an example of exposing a mixture comprising delta-9-tetrahydrocannabinol and one or more additional cannabinoids (e.g., delta-8-tetrahydrocannabinol, cannabidiol, etc.) to a heterogeneous liquid mixture. As shown in FIG. 1A, mixture 12 comprising delta-9-tetrahydrocannabinol 14 and one or more additional cannabinoids 16 is exposed to heterogeneous liquid mixture 20. Heterogeneous liquid mixture 20 may comprise two or more immiscible liquid phases, e.g., such as first liquid phase 22 and second liquid phase 24.

The first liquid phase and the second liquid phase may be present in the heterogeneous liquid mixture in any of a variety of mass ratios. For example, in some embodiments, a mass ratio of the first liquid phase to the second liquid phase in the mixture may be greater than or equal to 5:95, greater than or equal to 10:90, greater than or equal to 20:80, greater than or equal to 30:70, greater than or equal to 40:60, greater than or equal to 50:50, greater than or equal to 60:40, greater than or equal to 70:30, greater than or equal to 80:20, or greater than or equal to 90:10. In some embodiments, a mass ratio of the first liquid phase to the second liquid phase in the mixture may be less than or equal to 95:5, less than or equal to 90:10, less than or equal to 80:20, less than or equal to 70:30, less than or equal to 60:40, less than or equal to 50:50, less than or equal to 40:60, less than or equal to 30:70, less than or equal to 20:80, or less than or equal to 10:90. Combinations of the above-referenced ranges are also possible (e.g., greater than or equal to 5:95 and less than or equal to 95:5). Other ranges are also possible. As would be understood by one of ordinary skill in the art, when a mass ratio of A:B is "greater than or equal to 10:90," it means that, when the mass of component A that is present is divided by the mass of component B that is present, the resulting value is greater than or equal to 10/90 (i.e., greater than or equal to 0.111 repeating). Similarly, when a mass ratio of A:B is "less than or equal to 90:10," it that means that, when the mass of component A that is present is divided by the mass of component B that is present, the resulting value is less than or equal to 90/10 (i.e., less than or equal to 9).

The first liquid phase can be, in some embodiments, water soluble. In some embodiments, the first liquid phase may comprise at least one (e.g., at least one, at least two, at least three, etc.) liquid(s) comprising an amide group. As used herein, a liquid comprising an amide group is also generally referred to as "an amide-containing liquid." The first liquid phase, in some embodiments, may be miscible with water. In some embodiments, the first liquid phase comprises a polar aprotic solvent comprising an amide group.

The first liquid phase may comprise any of variety of appropriate amide-containing liquids. In some embodiments, the first liquid phase includes at least one liquid having a chemical structure shown in formula (VIII):

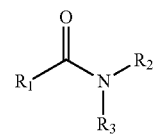

(VIII)

where $R_1$ is selected from hydrogen and $C_{1-4}$ aliphatic having a total of 1 to 4 carbon atoms, and where $R_2$ and $R_3$ can be the same or different and each is independently selected from hydrogen and $C_{1-4}$ aliphatic having a total of 1 to 4 carbon atoms. In some embodiments, the first liquid phase comprises at least one liquid having a chemical structure shown in formula (VIII) where $R_1$ is selected from hydrogen, $C_{1-4}$ alkyl having a total of 1 to 4 carbon atoms, $C_{1-4}$ alkenyl having a total of 1 to 4 carbon atoms, and $C_{1-4}$ alkyl having a total of 1 to 4 carbon atoms, and where $R_2$ and $R_3$ can be the same or different and each is independently selected from hydrogen, $C_{1-4}$ alkyl having a total of 1 to 4 carbon atoms, $C_{1-4}$ alkenyl having a total of 1 to 4 carbon atoms, and $C_{1-4}$ alkyl having a total of 1 to 4 carbon atoms. In some embodiments, the first liquid phase comprises at least one liquid having a chemical structure shown in formula (VIII) where $R_1$ is selected from hydrogen and $C_{1-4}$ alkyl having a total of 1 to 4 carbon atoms, and where $R_2$ and $R_3$ can be the same or different and each is independently selected from hydrogen and $C_{1-4}$ alkyl having a total of 1 to 4 carbon atoms. In some embodiments, the first liquid phase comprises at least one liquid having a chemical structure shown in formula (VIII) where $R_1$ is selected from hydrogen and $C_{1-4}$ alkyl having a total of 1 to 4 carbon atoms, and where $R_2$ and $R_3$ can be the same or different and each is independently selected from hydrogen and $C_{1-3}$ alkyl having a total of 1 to 3 carbon atoms.

Specific non-limiting examples of amide-containing liquids include formamide, acetamide, propanamide, butanamide, dimethyl formamide, diethyl formamide, dibutyl formamide, methyl formamide, dimethyl acetamide, diethyl acetamide, dimethyl propanamide, diethyl propanamide, dimethyl butanamide, and/or diethyl butanamide.

In some embodiments, the first liquid phase is a mixture comprising at least two (e.g., at least three, at least four, etc.) amide-containing liquids. For example, the first liquid phase may comprise an amide-containing liquid of a first type and an amide-containing liquid of a second type. In some embodiments, the amide-containing liquid of a first type has a lower polarity compared to the amide-containing liquid of a second type. An amide-containing liquid of a first type may have a structure as shown in formula (VIII), where $R_1$ is selected from hydrogen and $C_{1-4}$ aliphatic having 1 to 4 total carbon atoms, and where each of $R_2$ and $R_3$ is a hydrogen. In some embodiments, an amide-containing liquid of a first type may have a structure as shown in formula (VIII), where $R_1$ is selected from hydrogen and $C_{1-4}$ alkyl having 1 to 4 total carbon atoms, and where each of $R_2$ and $R_3$ is a hydrogen. In some embodiments, the first liquid phase may comprise two or more amide-containing liquids of a first type.

An amide-containing liquid of a second type may have a structure as shown in formula (VIII), where $R_1$ is selected from hydrogen and $C_{1-4}$ aliphatic having 1 to 4 total carbon atoms, and where $R_2$ and $R_3$ can be the same or different and each is independently a $C_{1-4}$ aliphatic having 1 to 4 total carbon atoms. For example, in some embodiments, an amide-containing liquid of a second type may have a structure as shown in formula (VIII), where $R_1$ is selected from hydrogen and $C_{1-4}$ alkyl having 1 to 4 total carbon atoms, and where $R_2$ and $R_3$ can be the same or different and each is independently a $C_{1-4}$ alkyl having 1 to 4 total carbon atoms. Alternatively or additionally, in some embodiments, an amide-containing liquid of a second type may have a structure as shown in formula (VIII), where $R_1$ is selected from hydrogen and $C_{1-4}$ aliphatic having 1 to 4 total carbon atoms, and where $R_2$ and $R_3$ are different and each is independently selected from a hydrogen and a $C_{1-4}$ aliphatic having 1 to 4 total carbon atoms. For example, an amide-containing liquid of a second type may have a structure as shown in formula (VIII), where $R_1$ is selected from hydrogen and $C_{1-4}$ alkyl having 1 to 4 total carbon atoms, and where $R_2$ and $R_3$ are different and each is independently selected from a hydrogen and a $C_{1-4}$ alkyl having 1 to 4 total carbon atoms. In some embodiments, the first liquid phase may comprise two or more amide-containing liquids of a second type.

Non-limiting examples of the amide-containing liquid of a first type include formamide, acetamide, propanamide, and/or butanamide. Non-limiting examples of the amide-containing liquid of a second type include dimethyl formamide, diethyl formamide, dibutyl formamide, methyl formamide, dimethyl acetamide, diethyl acetamide, dimethyl propanamide, diethyl propanamide, dimethyl butanamide, and/or diethyl butanamide.

In embodiments in which the first liquid phase is a mixture comprising an amide-containing liquid of a first type (e.g., formamide) and an amide-containing liquid of a second type (e.g., dimethylformamide), the two types of amide-containing liquid may be present in any of a variety of appropriate mass ratios. For example, in some embodiments, a mass ratio of the amide-containing liquid of a first type (e.g., formamide) to the amide-containing liquid of a second type (e.g., dimethylformamide) in the mixture may be greater than or equal to 20:80, greater than or equal to 30:70, greater than or equal to 33.3:66.6, greater than or equal to 40:60, greater than or equal to 45:55, greater than or equal to 50:50, greater than or equal to 55:45, greater than or equal to 60:40, greater than or equal to 66.6:33.3, or greater than or equal to 70:30. In some embodiments, a mass ratio of the amide-containing liquid of a first type (e.g., formamide) to the amide-containing liquid of a second type (e.g., dimethylformamide) in the mixture may be less than or equal to 80:20, less than or equal to 70:30, less than or equal to 66.6:33.3, less than or equal to 60:40, less than or equal to 55:45, less than or equal to 50:50, less than or equal to 45:55, less than or equal to 40:60, less than or equal to 33.3:66.6, or less than or equal to 30:70. Combinations of the above-referenced ranges are also possible (e.g., greater than or equal to 20:80 and less than or equal to 80:20, or greater than or equal to 40:60 and less than or equal to 60:40). Other ranges are also possible.

In some embodiments, the first liquid may comprise more than one amide-containing liquid of a first type and more than one amide-containing liquids of a second type. For example, as a non-limiting embodiment, the first liquid may comprise an amide-containing liquid of a first type (e.g., formamide) and a mixture of two amide-containing liquids of a second type (e.g., dimethyl formamide and dibutyl formamide).

In accordance with certain embodiments, the heterogeneous liquid mixture comprises a second liquid phase. The second liquid phase can be, in accordance with some embodiments, a water insoluble organic phase. The second liquid phase, in certain embodiments, comprises at least one (e.g., at least two, at least three, etc.) aliphatic hydrocarbon(s). As used herein, the term "aliphatic" refers to alkyl, alkenyl, alkynyl, and carbocyclic groups. The term "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, the second liquid phase comprises a $C_{3-20}$ aliphatic hydrocarbon having a total of 3 to 20 carbon atoms. For example, "$C_{3-20}$ aliphatic" may encompass, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{3-20}$, $C_{3-18}$, $C_{3-16}$, $C_{3-14}$, $C_{3-12}$, $C_{3-10}$, $C_{3-8}$, $C_{3-6}$, $C_{3-4}$, $C_{4-20}$, $C_{4-18}$, $C_{4-16}$, $C_{4-14}$, $C_{4-12}$, $C_{4-10}$, $C_{4-8}$, $C_{4-6}$, $C_{4-5}$, $C_{6-20}$, $C_{6-18}$, $C_{6-16}$, $C_{6-14}$, $C_{6-12}$, $C_{6-10}$, $C_{6-8}$, $C_{6-7}$, $C_{8-20}$, $C_{8-18}$, $C_{8-16}$, $C_{8-14}$, $C_{8-12}$, $C_{8-10}$, $C_{8-9}$, $C_{10-20}$, $C_{10-18}$, $C_{10-16}$, $C_{10-14}$, $C_{10-12}$, $C_{10-11}$, $C_{12-20}$, $C_{12-18}$, $C_{12-16}$, $C_{12-14}$, $C_{12-13}$, $C_{14-20}$, $C_{14-18}$, $C_{14-16}$, $C_{14-15}$, $C_{16-20}$, $C_{16-18}$, $C_{16-17}$, $C_{18-20}$, $C_{18-19}$, and $C_{19-20}$ aliphatic. In some embodiments, the $C_{3-20}$ aliphatic hydrocarbon is branched or unbranched, saturated or unsaturated, acyclic or cyclic. In some embodiments, the $C_{3-20}$ aliphatic hydrocarbon comprises an alkyl, an alkenyl, an alkynyl, a cycloalkyl, a cycloalkenyl, and/or a cycloalkynyl group having a total of 3 to 20 carbon atoms. In some embodiments, the aliphatic hydrocarbon is unsubstituted and/or does not include a heteroatom. For example, in some embodiments, a liquid of the second liquid phase does not include a substituted aliphatic hydrocarbon and/or a heteroaliphatic hydrocarbon, e.g., an aliphatic hydrocarbon comprising at least one heteroatom. In some embodiments, a liquid of the second liquid phase comprises a $C_{3-20}$ aliphatic hydrocarbon that is immiscible with the first liquid phase.

The second liquid phase may include any of a variety of suitable $C_{3-20}$ aliphatic hydrocarbons. Non-limiting examples of $C_{3-20}$ aliphatic hydrocarbons that can be used in the second liquid phase include alkanes, alkenes, alkynes, cycloalkanes, cycloalkene, cycloalkene, and/or cycloalkynes. Non-limiting examples of liquids that can be used in the second liquid phase include pentane, pentene, pentyne, cyclopentane, cyclopentene, cyclopentyne, hexane, hexene, hexyne, cyclohexane, cyclohexene, cyclohexyne, heptane, heptene, heptyne, cycloheptane, cycloheptene, cycloheptyne, dodecane, dodecene, dodecyne, cyclododecane, cyclododecene, and/or cyclododecyne.

Certain embodiments of the present disclosure comprise separating delta-9-tetrahydrocannabinol from one or more additional cannabinoids (e.g., delta-8-tetrahydrocannabinol, cannabidiol, etc.) using a heterogeneous liquid mixture, such as any of the mixtures described above or elsewhere herein.

In association with certain of the embodiments described herein, certain liquids are said to be "enriched" in a first solute or a second solute, relative to another liquid. In this context, a first liquid is said to be "enriched" in the first solute relative to a second liquid if the mole fraction of the first solute relative to the sum of the first solute and the second solute in the first liquid is higher than the mole fraction of the first solute relative to the sum of the first solute and the second solute in the second liquid. Similarly, a first liquid is said to be "enriched" in the second solute relative to a second liquid if a mole fraction of the second solute relative to the sum of the first solute and the second solute in the first liquid is higher than a mole fraction of the second solute relative to the sum of the first solute and the second solute in the second liquid. In some instances in which a first liquid is enriched in a solute relative to a second liquid, it is particularly advantageous if the concentration of the solute in the first liquid is higher than the concentration of that solute in the second liquid. For example, in some embodiments, it is particularly advantageous if a separation process produces (1) a first liquid that has a higher concentration of first solute (e.g., delta-9-tetrahydrocannabinol) than the concentration of the first solute in the initial mixture and (2) a second liquid that has a higher concentration of second solute (e.g., delta-8-tetrahydrocannabinol and/or other cannabinoids that are not delta-9-tetrahydrocannabinol) than the concentration of the second solute in the initial mixture.

In certain embodiments, the method for separating delta-9-tetrahydrocannabinol from delta-8-tetrahydrocannabinol comprises exposing a the mixture comprising the delta-9-tetrahydrocannabinol and the delta-8-tetrahydrocannabinol to a heterogeneous liquid mixture such that the mole fraction of the delta-9-tetrahydrocannabinol relative to the sum of the delta-9-tetrahydrocannabinol and the delta-8-tetrahydrocannabinol in the first liquid phase is greater than the mole fraction of the delta-9-tetrahydrocannabinol relative to the sum of the delta-9-tetrahydrocannabinol and the delta-8-tetrahydrocannabinol in the mixture. In some embodiments, the mole fraction of the delta-9-tetrahydrocannabinol relative to the sum of the delta-9-tetrahydrocannabinol and the delta-8-tetrahydrocannabinol in the first liquid phase is at least 10% (or at least 25%, at least 50%, at least 100%, at least 1000%, or more) greater than the mole fraction of the delta-9-tetrahydrocannabinol relative to the sum of the delta-9-tetrahydrocannabinol and the delta-8-tetrahydrocannabinol in the mixture.

In addition, in some such embodiments, the mole fraction of the delta-8-tetrahydrocannabinol relative to the sum of the delta-8-tetrahydrocannabinol and the delta-9-tetrahydrocannabinol in the second liquid phase is greater than the mole fraction of the delta-8-tetrahydrocannabinol relative to the sum of the delta-8-tetrahydrocannabinol and the delta-9-tetrahydrocannabinol in the mixture. In some embodiments, the mole fraction of the delta-8-tetrahydrocannabinol relative to the sum of the delta-8-tetrahydrocannabinol and the delta-9-tetrahydrocannabinol in the second liquid phase is at least 10% (or at least 25%, at least 50%, at least 100%, at least 1000%, or more) greater than the mole fraction of the delta-8-tetrahydrocannabinol relative to the sum of the delta-8-tetrahydrocannabinol and the delta-9-tetrahydrocannabinol in the mixture.

To calculate a mole fraction of a first solute relative to the sum of the first solute and the second solute in a particular liquid, one would divide the number of moles of the first solute present in the liquid by the sum of the number of moles of the first solute present in the liquid and the number of moles of the second solute present in the liquid. This is shown mathematically as follows:

$$x_1 = \frac{n_1}{n_1 + n_2}$$

where $x_1$ is the mole fraction of the first solute relative to the sum of the first solute and the second solute in the liquid, $n_1$ is the number of moles of the first solute in the liquid, and $n_2$ is the number of moles of the second solute in the liquid. Similarly, to calculate a mole fraction of a second solute relative to the sum of the first solute and the second solute in a particular liquid, one would divide the number of moles of the second solute present in the liquid by the sum of the number of moles of the first solute present in the liquid and the number of moles of the second solute present in the liquid. This is shown mathematically as follows:

$$x_2 = \frac{n_2}{n_1 + n_2}$$

where $x_2$ is the mole fraction of the second solute relative to the sum of the first solute and the second solute in the liquid, $n_1$ is the number of moles of the first solute in the liquid, and $n_2$ is the number of moles of the second solute in the liquid.

In some embodiments, the separating may occur as a result of preferential association of the delta-9-tetrahydrocannabinol and the one or more additional cannabinoids with different liquid phases of the heterogeneous liquid mixture. For example, in some embodiments, upon exposing the mixture to the heterogeneous liquid mixture, the delta-9-tetrahydrocannabinol preferentially associates with the first liquid phase, while the one or more additional cannabinoids preferentially associate with the second liquid phase. In some such embodiments, after the preferential associations, the first liquid phase becomes enriched in the delta-9-tetrahydrocannabinol, while the second liquid phase becomes enriched in the one or more additional cannabinoids.

Figure 1B:
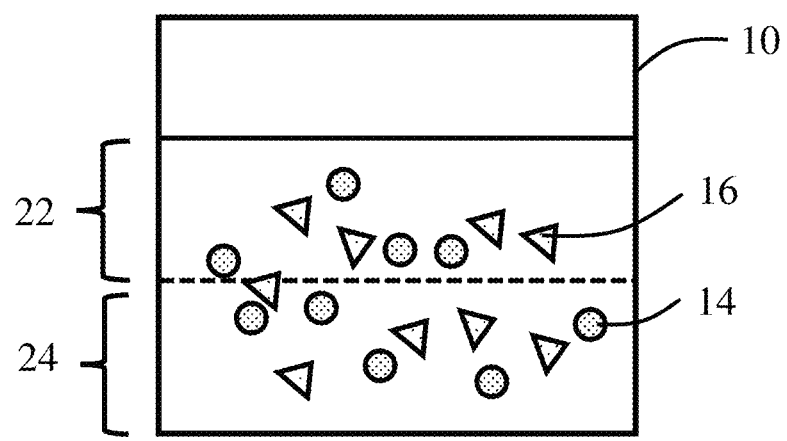
Figure 1C:
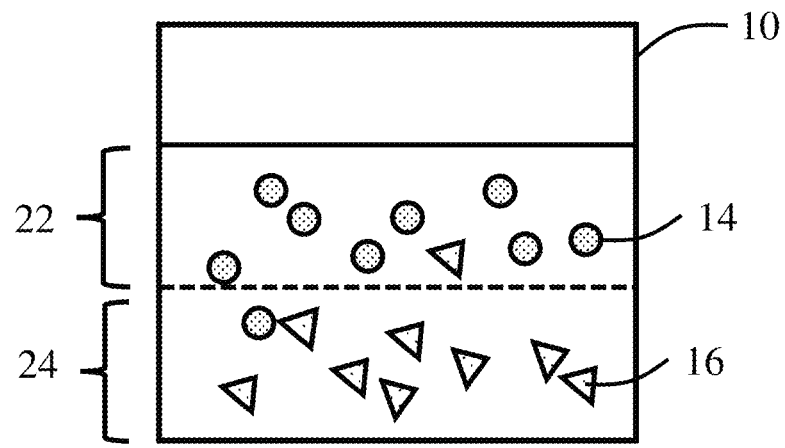

FIGS. 1B-1C illustrate an example of the preferential association of the delta-9-tetrahydrocannabinol and the one or more additional cannabinoids (e.g., delta-8-tetrahydrocannabinol, cannabidiol, etc.) into separate liquid phases. As shown in FIG. 1B, the mixture comprising delta-9-tetrahydrocannabinol 14 and one or more additional cannabinoids 16 has been disposed in heterogeneous liquid mixture 20 comprising first liquid phase 22 and second liquid phase 24. As shown in FIG. 1C, delta-9-tetrahydrocannabinol 14 has preferentially associated with first liquid phase 22, while one or more additional cannabinoids 16 have preferentially associated with second liquid phase 24. After the preferential association, first liquid phase 22 is enriched in delta-9-tetrahydrocannabinol 14 and second liquid phase 24 is enriched in the one or more additional cannabinoids 16.

In some embodiments, an increase in a molar ratio and/or a preferential association of the chemical species (e.g., the delta-9-tetrahydrocannabinol and the one or more additional cannabinoids) with their respective liquid phases (e.g., the first liquid phase, the second liquid phase) in the heterogeneous liquid mixture is related to the ability of the chemical species to selectively partition into the different liquid phases. For example, in a biphasic heterogeneous liquid mixture comprising a first liquid phase and a second liquid phase, a partition coefficient $K_n$ may be defined for each chemical species as a measure of its ability to partition between the first liquid phase and the second liquid phase at equilibrium. For chemical species i, the partition coefficient $K_i$ may be expressed as: $K_i = C_{i\ (1st\ liquid\ phase)} / C_{i\ (2nd\ liquid\ phase)}$, which is a ratio of the concentration of chemical species i in the first liquid phase ($C_{i,\ 1st\ liquid\ phase}$) to the concentration of chemical species i in the second liquid phase ($C_{i,\ 2st\ liquid\ phase}$). In the context of the present disclosure, chemical species i may refer to delta-9-tetrahydrocannabinol or any of the one or more additional cannabinoids. The concentration of chemical species is generally expressed in terms of molarity (i.e., M, or moles per liter).

For example, in embodiments in which the mixture comprises the delta-9-tetrahydrocannabinol and the one or more additional cannabinoids, the delta-9-tetrahydrocannabinol may have a partition coefficient $K_{d9,THC}$, which, as described above, is expressed as a ratio of the concentration of the delta-9-tetrahydrocannabinol in the first liquid phase to the concentration of the delta-9-tetrahydrocannabinol in the second liquid phase at equilibrium (e.g., $K_{d9,THC} = C_{d9,\ THC\ (1st\ liquid\ phase)} / C_{d9,\ THC\ (2nd\ liquid\ phase)}$). Similarly, each of the one or more additional cannabinoids may individually have and/or collectively have a partition coefficient $K_{cnbd,\ i}$, where $K_{cnbd,\ i}$ is expressed as a ratio of the concentration of the one or more additional cannabinoids in the first liquid phase to the concentration of the one or more additional cannabinoids in the second liquid phase (e.g., $K_{cnbd,\ i} = C_{cnbd,\ i\ (1st\ liquid\ phase)} / C_{cnbd,\ i\ (2nd\ liquid\ phase)}$). For example, in embodiments in which the one or more additional cannabinoids comprise delta-8-tetrahydrocannabinol, a partition coefficient $K_{d8,\ THC}$ for the delta-8-tetrahydrocannabinol between the first liquid phase and the second liquid phase may be expressed a ratio of the concentration of the delta-8-tetrahydrocannabinol in the first liquid phase to the concentration of the delta-8-tetrahydrocannabinol in the second liquid phase (e.g., $C_{d8,\ THC\ (1st\ liquid\ phase)} / C_{d8,\ THC\ (2nd\ liquid\ phase)}$). As another example, in embodiments in which the one or more additional cannabinoids comprise cannabidiol, a partition coefficient $K_{CBD}$ for cannabidiol between the first liquid phase and the second liquid phase may be expressed as a ratio of the concentration of the cannabidiol in the first liquid phase to the concentration of the cannabidiol in the second liquid phase (e.g., $C_{CBD\ (1st\ liquid\ phase)} / C_{CBD\ (2nd\ liquid\ phase)}$). The ranges described herein for the partition coefficient of $K_{cnbd,\ i}$ between the first liquid phase and the second liquid phase may, in certain embodiments, be the partition coefficient of delta-8-tetrahydrocannabinol ($K_{d8,\ THC}$) between the first liquid phase and the second liquid phase, the partition coefficient of cannabidiol ($K_{CBD}$) between the first liquid phase and the second liquid phase may, and/or the partition coefficient of any other cannabinoid that is not delta-8-tetrahydrocannabinol between the first liquid phase and the second liquid phase.

The delta-9-tetrahydrocannabinol may have any of a variety of appropriate partition coefficients $K_{d9,THC}$ between the first liquid phase and the second liquid phase. In some embodiments, the delta-9-tetrahydrocannabinol may have a partition coefficient $K_{d9,THC}$ between the first liquid phase and the second liquid phase of greater than or equal to 0.1, greater than or equal to 0.2, greater than or equal to 0.3, greater than or equal to 0.5, greater than or equal to 0.75, greater than or equal to 1, greater than or equal to 1.05, greater than or equal to 1.1, greater than or equal to 1.15, greater than or equal to 1.2, greater than or equal to 1.25, greater than or equal to 1.3, greater than or equal to 1.4, greater than or equal to 1.6, greater than or equal to 1.8, or greater than or equal to 2. In some embodiments, the delta-9-tetrahydrocannabinol may have a partition coefficient $K_{d9,THC}$ between the first liquid phase and the second liquid phase of up to 2.5, up to 3, up to 4, up to 5, up to 6, up to 8, up to 10, or greater. Combinations of the above-referenced ranges are possible (e.g., greater than or equal to 0.1 and up to 10).

The one or more cannabinoids other than delta-9-tetrahydrocannabinol (e.g., delta-8-tetrahydrocannabinol, cannabidiol, etc.) may have any of a variety of appropriate partition coefficients $K_{cnbd,i}$ (e.g., $K_{d8,THC}$, $K_{CBD}$, etc.) between the first liquid phase and the second liquid phase. In some embodiments, the one or more cannabinoids other than delta-9-tetrahydrocannabinol may have a partition coefficient $K_{cnbd,i}$ between the first liquid phase and the second liquid phase of less than or equal to 200, less than or equal to 150, less than or equal to 100, less than or equal to 50, less than or equal to 25, less than or equal to 10, less than or equal to 8, less than or equal to 6, less than or equal to 4, less than or equal to 3, less than or equal to 2, less than or equal to 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, or less than or equal to 0.2 (and/or down to 0.01, down to 0.001, or less). For example, in some embodiments, $K_{d8,THC}$ between the first liquid phase and the second liquid phase is less than or equal to 2, less than or equal to 1.8, less than or equal to 1.6, less than or equal to 1.5, less than or equal to 1.4, less than or equal to 1.2, less than or equal to 1.1, less than or equal to 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, or less than or equal to 0.2 (and/or down to 0.1 or less). As another example, in some embodiments, $K_{CBD}$ between the first liquid phase and the second liquid phase is less than or equal to 200, less than or equal to 150, less than or equal to 100, less than or equal to 50, less than or equal to 25, less than or equal to 10, less than or equal to 8, less than or equal to 6, less than or equal to 4, less than or equal to 3, less than or equal to 2, less than or equal to 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, or less than or equal to 0.2 (and/or down to 0.01, down to 0.001, or less). In certain embodiments, for each cannabinoid in the mixture that is not delta-9-tetrahydrocannabinol and is not delta-8-tetrahydrocannabinol, the partition coefficient K between the first liquid phase and the second liquid phase for that cannabinoid is less than or equal to 200, less than or equal to 150, less than or equal to 100, less than or equal to 50, less than or equal to 25, less than or equal to 10, less than or equal to 8, less than or equal to 6, less than or equal to 4, less than or equal to 3, less than or equal to 2, less than or equal to 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, or less than or equal to 0.2 (and/or down to 0.01, down to 0.001, or less).

In some embodiments, it may be advantageous to select a heterogeneous liquid mixture having a relatively high ratio of the partition coefficient $K_{d9,THC}$ of the delta-9-tetrahydrocannabinol to the partition coefficient $K_{cnbd, i}$ (e.g., $K_{d8, THC}$, $K_{CBD}$, etc.) of the one or more additional cannabinoids (e.g., delta-8-tetrahydrocannabinol, cannabidiol, etc.). A heterogeneous liquid mixture having a relatively high ratio of $K_{d9,THC}$ to $K_{cnbd, i}$ may lead to a more efficient association of the delta-9-tetrahydrocannabinol with the first liquid phase, and similarly, a more efficient association of the one or more additional cannabinoids with the second liquid phase. For example, in a heterogeneous liquid mixture having a relatively high $K_{d9,THC}$ to $K_{cnbd, i}$ ratio (e.g., as described below), the delta-9-tetrahydrocannabinol may exhibit a higher selectivity towards the first liquid phase compared to the one of more additional cannabinoids, and thereby result in a more efficient partitioning of the delta-9-tetrahydrocannabinol into the first liquid phase.

In some embodiments, the ratio of the partition coefficient $K_{d9,THC}$ of the delta-9-tetrahydrocannabinol to the partition coefficient $K_{cnbd, i}$ (e.g., $K_{d8,THC}$, $K_{CBD}$) of the one or more additional cannabinoids (e.g., delta-8-tetrahydrocannabinol, cannabidiol, etc.) is greater than 1, greater than or equal to 1.05, greater than or equal to 1.1, greater than or equal to 1.15, greater than or equal to 1.2, greater than or equal to 1.25, greater than or equal to 1.3, greater than or equal to 1.35, greater than or equal to 1.4, greater than or equal to 1.5, greater than or equal to 2, greater than or equal to 3, greater than or equal to 5, greater than or equal to 10, greater than or equal to 50, or greater than or equal to 100 (and/or, in some embodiments, less than or equal to 100, less than or equal to 50, less than or equal to 10, less than or equal to 5, less than or equal to 3, less than or equal to 2, less than or equal to 1.5, less than or equal to 1.4, less than or equal to 1.35, less than or equal to 1.3, less than or equal to 1.25, or less). Combinations of the above-referenced ranges are possible (e.g., greater than 1 and less than or equal to 100, greater than or equal to 1.25 and less than or equal to 100, or greater than or equal to 1.3 and less than or equal to 100).

For example, in some embodiments, the ratio of the partition coefficient $K_{d9,THC}$ of the delta-9-tetrahydrocannabinol to the partition coefficient $K_{d8,THC}$ of the delta-8-tetrahydrocannabinol is greater than 1, greater than or equal to 1.05, greater than or equal to 1.1, greater than or equal to 1.15, greater than or equal to 1.2, greater than or equal to 1.25, greater than or equal to 1.3, greater than or equal to 1.35, greater than or equal to 1.4, greater than or equal to 1.5, greater than or equal to 2, greater than or equal to 3, greater than or equal to 5, or greater than or equal to 10 (and/or, in some embodiments, less than or equal to 10, less than or equal to 5, less than or equal to 3, less than or equal to 2, less than or equal to 1.5, less than or equal to 1.4, less than or equal to 1.35, less than or equal to 1.3, less than or equal to 1.25, or less). Combinations of the above-referenced ranges are possible (e.g., greater than 1 and less than or equal to 10, greater than or equal to 1.25 and less than or equal to 10, or greater than or equal to 1.3 and less than or equal to 10).

As another example, in some embodiments, the ratio of the partition coefficient $K_{d9,THC}$ of the delta-9-tetrahydrocannabinol to the partition coefficient $K_{CBD}$ of cannabidiol is greater than 1, greater than or equal to 1.05, greater than or equal to 1.1, greater than or equal to 1.15, greater than or equal to 1.2, greater than or equal to 1.25, greater than or equal to 1.3, greater than or equal to 1.35, greater than or equal to 1.4, greater than or equal to 1.5, greater than or equal to 2, greater than or equal to 3, greater than or equal to 5, greater than or equal to 10, greater than or equal to 50, or greater than or equal to 100 (and/or, in some embodiments, less than or equal to 100, less than or equal to 50, less than or equal to 10, less than or equal to 5, less than or equal to 3, less than or equal to 2, less than or equal to 1.5, less than or equal to 1.4, less than or equal to 1.35, less than or equal to 1.3, less than or equal to 1.25, or less). Combinations of the above-referenced ranges are possible (e.g., greater than 1 and less than or equal to 100, greater than or equal to 1.25 and less than or equal to 100, or greater than or equal to 1.3 and less than or equal to 100).

In some embodiments, for each cannabinoid in the mixture that is not the delta-9-tetrahydrocannabinol and is not delta-8-tetrahydrocannabinol, the ratio of the partition coefficient $K_{d9,THC}$ of the delta-9-tetrahydrocannabinol to the partition coefficient K of that cannabinoid that is not delta-9-tetrahydrocannabinol and is not delta-8-tetrahydrocannabinol is greater than 1, greater than or equal to 1.05, greater than or equal to 1.1, greater than or equal to 1.15, greater than or equal to 1.2, greater than or equal to 1.25, greater than or equal to 1.3, greater than or equal to 1.35, greater than or equal to 1.4, greater than or equal to 1.5, greater than or equal to 2, greater than or equal to 3, greater than or equal to 5, greater than or equal to 10, greater than or equal to 50, or greater than or equal to 100 (and/or, in some embodiments, less than or equal to 100, less than or equal to 50, less than or equal to 10, less than or equal to 5, less than or equal to 3, less than or equal to 2, less than or equal to 1.5, less than or equal to 1.4, less than or equal to 1.35, less than or equal to 1.3, less than or equal to 1.25, or less). Combinations of the above-referenced ranges are also possible (e.g., greater than 0.01 and less than or equal to 100, greater than or equal to 1.25 and less than or equal to 100, or greater than or equal to 1.3 and less than or equal to 100). Other ranges are also possible.

In some embodiments, it may be particularly advantageous to select a heterogeneous liquid mixture having a delta-9-tetrahydrocannabinol partition coefficient $K_{d9,THC}$ of greater than 1 and a partition coefficient $K_{cnbd,i}$ (e.g., $K_{d8, THC}$, $K_{CBD}$, etc.) of less than 1 for the one or more additional cannabinoids (e.g., delta-8-tetrahydrocannabinol, cannabidiol, etc.) or vice versa. In some such embodiments, the delta-9-tetrahydrocannabinol may preferentially partition to the first liquid phase over the second liquid phase, and the one or more additional cannabinoids may preferentially partition to the second liquid phase over the first liquid phase. Such a combination of partition coefficients may result in a higher extraction efficiency of the delta-9-tetrahydrocannabinol and may be associated with certain operational advantages (e.g., need for less solvent, lower number of extraction stages, etc.). For example, in some embodiments, the delta-9-tetrahydrocannabinol may have a partition coefficient $K_{d9,THC}$ between the first liquid phase and the second liquid phase of greater than 1, greater than or equal to 1.05, greater than or equal to 1.1, greater than or equal to 1.15, greater than or equal to 1.2, greater than or equal to 1.25, greater than or equal to 1.3, greater than or equal to 1.4, greater than or equal to 1.6, greater than or equal to 1.8, greater than or equal to 2, or greater (and/or, in some embodiments, up to 2.5, up to 3, up to 4, up to 5, up to 6, up to 8, or up to 10, or more). Combinations of the above-referenced ranges are possible (e.g., greater than 1 and up to 10). Other ranges are also possible. Additionally, in some embodiments, the one or more additional cannabinoids (e.g., delta-8-tetrahydrocannabinol, cannabidiol, etc.) may have a partition coefficient $K_{cnbd,i}$ (e.g., $K_{d8,THC}$, $K_{CBD}$) between the first liquid phase and the second liquid phase of less than 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, less than or equal to 0.2, less than or equal to 0.1, or less (and/or down to 0.01, down to 0.001, or less). Combinations of the above-referenced ranges are possible. Other ranges are also possible.

For example, in some embodiments, the delta-8-tetrahydrocannabinol may have a partition coefficient ($K_{d8,THC}$) between the first liquid phase and the second liquid phase of less than 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, less than or equal to 0.2, less than or equal to 0.1, or less (and/or down to 0.01, down to 0.001, or less). As another example, in some embodiments, the cannabidiol may have a partition coefficient ($K_{CBD}$) between the first liquid phase and the second liquid phase of less than 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, less than or equal to 0.2, less than or equal to 0.1, or less (and/or down to 0.01, down to 0.001, or less). In some embodiments, for each cannabinoid in the mixture that is not the delta-9-tetrahydrocannabinol, the partition coefficient K of that cannabinoid that is not delta-9-tetrahydrocannabinol is less than 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, less than or equal to 0.2, less than or equal to 0.1, or less (and/or down to 0.01, down to 0.001, or less). Combinations of the above-referenced ranges are possible. Other ranges are also possible.

In some embodiments, it may be advantageous to select a heterogeneous liquid mixture having a particular combination of partition coefficients (e.g., $K_{d9,THC}$, $K_{cnbd,i}$) and/or a particular ratio of between the partition coefficients (e.g., $K_{d9,THC}/K_{cnbd,i}$) in one or more of the ranges referenced above. For example, in some embodiments, it may be desirable to select a heterogeneous liquid mixture having a relatively high $K_{d9,THC}/K_{cnbd,i}$ ratio (e.g., greater than 1.1, greater than or equal to 1.25, or greater than or equal to 1.3) and/or a heterogeneous liquid mixture having a particular combination of partition coefficients (e.g., a $K_{d9,THC}$ that is greater than 1 and a $K_{cnbd,i}$ that is less than 1 or vice versa).

The above-referenced partition coefficients (e.g., $K_{d9,THC}$, $K_{cnbd,i}$) of various cannabinoids and/or ratios thereof (e.g., $K_{d9,THC}/K_{cnbd,i}$) may be controlled by adjusting the types and/or relative amount of various liquids within the heterogeneous liquid mixture. For example, in embodiments in which the first liquid phase comprises a first amide-containing liquid (e.g., formamide) and a second amide-containing liquid (e.g., dimethyl formamide or methyl formamide), the relative amount (mass ratio of the of the two types of amide-containing liquid may be adjusted to vary the polarity of the first liquid phase, thereby establishing desirable partition coefficients of the various cannabinoids and/or the ratio thereof. Similarly, the type and amount of the first liquid phase and the second liquid phase may be adjusted to control the differential partitioning of various cannabinoids into different liquid phases.

Figure 1D:
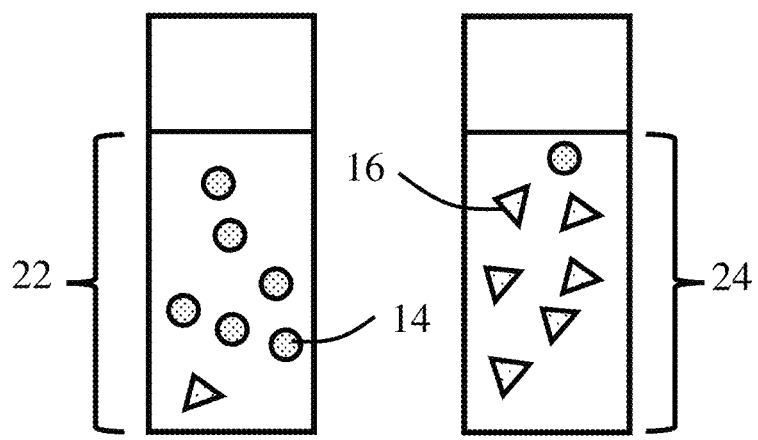

In some embodiments, the method comprises separating the delta-9-tetrahydrocannabinol that associated with the first liquid phase from the one or more additional cannabinoids (e.g., delta-8-tetrahydrocannabinol, cannabidiol, etc.) that associated with the second liquid phase. FIG. 1D illustrates an example of one such set of embodiments. As shown in FIG. 1D, first liquid phase 22 containing the preferentially associated delta-9-tetrahydrocannabinol 14 has been separated from second liquid phase 24 containing the preferentially associated one or more additional cannabinoids 16.

It should be understood that the term "separation," as used herein, does not necessarily mean complete and absolute separation, but is used herein as to refer to the production of a liquid phase that is enriched in at least one of the components within the original mixture. In some embodiments, the "separation" of delta-9-tetrahydrocannabinol and another component can refer to the production of a liquid phase that is enriched in the delta-9-tetrahydrocannabinol relative to the amount of the delta-9-tetrahydrocannabinol and the other component in the original mixture (and, optionally, the production of a second liquid phase that is enriched in one or more additional cannabinoids that are not delta-9-tetrahydrocannabinol relative to the amount of the one or more additional cannabinoids and the delta-9-tetrahydrocannabinol in the original mixture).

In some embodiments, the separated first liquid phase (e.g., first liquid phase 22 shown in FIG. 1D) is enriched in delta-9-tetrahydrocannabinol relative to the amount of the delta-9-tetrahydrocannabinol in the original mixture (e.g., mixture 12 in FIG. 1A). For example, in some embodiments, the mole fraction of delta-9-tetrahydrocannabinol relative to all cannabinoids (including the delta-9-tetrahydrocannabinol and the one or more additional cannabinoids) in the first liquid phase may be at least 1.2 times, at least 1.5 times, at least 2 times, at least 3 times, at least 5 times, at least 10 times, at least 50 times, at least 100 times, or at least 1000 times (and/or up to $10^4$ times, up to $10^5$ times, or more) the mole fraction of delta-9-tetrahydrocannabinol relative to all cannabinoids in the original mixture. Combination of the above-referenced ranges are possible. Other ranges are also possible. As a non-limiting example, in some cases, the original mixture may contain 50 mol of delta-9-tetrahydrocannabinol and 100 mol total of all cannabinoids, which means the mole fraction of delta-9-tetrahydrocannabinol relative to all cannabinoids would be 0.5 (i.e., 50/100). After partitioning (via one or more stages), the first liquid phase may contain 45 mol of delta-9-tetrahydrocannabinol and 50 mol total of all cannabinoids, which means the mole fraction of delta-9-tetrahydrocannabinol relative to all cannabinoids in the first liquid phase would be 0.9 (i.e., 45/50). In this non-limiting example, the mole fraction of delta-9-tetrahydrocannabinol relative to all cannabinoids in the first liquid phase is 1.8 times the mole fraction of delta-9-tetrahydrocannabinol relative to all cannabinoids in the original mixture (because 0.9 divided by 0.5 is 1.8). In this example, the first liquid phase would be said to be enriched in delta-9-tetrahydrocannabinol relative to the original mixture because the mole fraction of delta-9-tetrahydrocannabinol relative to all cannabinoids in the first liquid phase is higher than the mole fraction of delta-9-tetrahydrocannabinol relative to all cannabinoids in the original mixture. As another non-limiting example, in some cases, the original mixture may contain 50 mol of delta-9-tetrahydrocannabinol and 100 mol total of all cannabinoids, which means the mole fraction of delta-9-tetrahydrocannabinol relative to all cannabinoids would be 0.5 (i.e., 50/100). After partitioning (via one or more stages), the second liquid phase may contain 5 mol of delta-9-tetrahydrocannabinol and 50 mol total of all cannabinoids, which means the mole fraction of delta-9-tetrahydrocannabinol relative to all cannabinoids in the second liquid phase would be 0.1 (i.e., 5/50). In this non-limiting example, the mole fraction of delta-9-tetrahydrocannabinol relative to all cannabinoids in the second liquid phase is 0.2 times the mole fraction of delta-9-tetrahydrocannabinol relative to all cannabinoids in the original mixture (because 0.1 divided by 0.5 is 0.2). In this example, the second liquid phase would not be said to be enriched in delta-9-tetrahydrocannabinol relative to the original mixture because the mole fraction of delta-9-tetrahydrocannabinol relative to all cannabinoids in the second liquid phase is lower than the mole fraction of delta-9-tetrahydrocannabinol relative to all cannabinoids in the original mixture.

In some embodiments, the mole fraction of delta-9-tetrahydrocannabinol relative to the total amount of delta-9-tetrahydrocannabinol and delta-8-tetrahydrocannabinol in the first liquid phase may be at least 1.2 times, at least 1.5 times, at least 2 times, at least 3 times, at least 5 times, at least 10 times, at least 50 times, at least 100 times, or at least 1000 times (and/or up to 104 times, up to 105 times, or more) the mole fraction of delta-9-tetrahydrocannabinol relative to the total amount of delta-9-tetrahydrocannabinol and delta-8-tetrahydrocannabinol in the original mixture. In some embodiments, the mole fraction of delta-9-tetrahydrocannabinol relative to the total amount of delta-9-tetrahydrocannabinol and cannabidiol in the first liquid phase may be at least 1.2 times, at least 1.5 times, at least 2 times, at least 3 times, at least 5 times, at least 10 times, at least 50 times, at least 100 times, or at least 1000 times (and/or up to $10^4$ times, up to $10^5$ times, or more) the mole fraction of delta-9-tetrahydrocannabinol relative to the total amount of delta-9-tetrahydrocannabinol and cannabidiol in the original mixture.

In some embodiments, the separated second liquid phase (e.g., second liquid phase 24 shown in FIG. 1D) is enriched in one or more additional cannabinoids (that are not delta-9-tetrahydrocannabinol) relative to the amount of the cannabinoids in the original mixture (e.g., mixture 12 in FIG. 1A). For example, in some embodiments, the mole fraction of the one or more additional cannabinoids relative to all cannabinoids in the second liquid phase may be at least 1.2 times, at least 1.5 times, at least 2 times, at least 3 times, at least 5 times, at least 10 times, at least 50 times, at least 100 times, or at least 1000 times (and/or up to $10^4$ times, up to $10^5$ times, or more) the mole fraction of the one or more additional cannabinoids relative to all cannabinoids in the original mixture. In some embodiments, the mole fraction of delta-8-tetrahydrocannabinol relative to all cannabinoids in the second liquid phase may be at least 1.2 times, at least 1.5 times, at least 2 times, at least 3 times, at least 5 times, at least 10 times, at least 50 times, at least 100 times, or at least 1000 times (and/or up to $10^4$ times, up to $10^5$ times, or more) the mole fraction of delta-8-tetrahydrocannabinol relative to all cannabinoids in the original mixture. In some embodiments, the mole fraction of cannabidiol relative to all cannabinoids in the second liquid phase may be at least 1.2 times, at least 1.5 times, at least 2 times, at least 3 times, at least 5 times, at least 10 times, at least 50 times, at least 100 times, at least 1000 times, or at least $10^5$ times (and/or up to $10^6$ times, up to $10^7$ times, up to $10^8$ times, or more) the mole fraction of cannabidiol relative to all cannabinoids in the original mixture. Combination of the above-referenced ranges are possible. Other ranges are also possible.

In some embodiments, the mole fraction of delta-8-tetrahydrocannabinol relative to the total amount of delta-8-tetrahydrocannabinol and delta-9-tetrahydrocannabinol in the second liquid phase may be at least 1.2 times, at least 1.5 times, at least 2 times, at least 3 times, at least 5 times, at least 10 times, at least 50 times, at least 100 times, at least 1000 times, or at least $10^5$ times (and/or up to $10^6$ times, up to 107 times, up to $10^8$ times, or more) the mole fraction of delta-8-tetrahydrocannabinol relative to the total amount of delta-8-tetrahydrocannabinol and delta-9-tetrahydrocannabinol in the original mixture. In some embodiments, the mole fraction of cannabidiol relative to the total amount of cannabidiol and delta-9-tetrahydrocannabinol in the second liquid phase may be at least 1.2 times, at least 1.5 times, at least 2 times, at least 3 times, at least 5 times, at least 10 times, at least 50 times, at least 100 times, or at least 1000 times (and/or up to $10^4$ times, up to $10^5$ times, or more) the mole fraction of cannabidiol relative to the total amount of cannabidiol and delta-9-tetrahydrocannabinol in the original mixture. Combination of the above-referenced ranges are possible. Other ranges are also possible.

In some embodiments, the method described herein may have a relatively high delta-9-tetrahydrocannabinol extraction efficiency. As used herein, the term "extraction efficiency" refers to the percentage of separated delta-9-tetrahydrocannabinol (e.g., delta-9-tetrahydrocannabinol that preferentially associates with the first liquid phase) relative to the total amount of delta-9-tetrahydrocannabinol in the mixture. For example, in some embodiments, the delta-9-tetrahydrocannabinol extraction efficiency may be greater than or equal to 80% (e.g., greater than or equal to 90%, greater than or equal to 95%, greater than or equal to 97%, greater than or equal to 98%, greater than or equal to 99%, greater than or equal to 99.5%, greater than or equal to 99.7%, greater than or equal to 99.9%, greater than or equal to 99.99%, or equal to 100%).

Figure 1E:
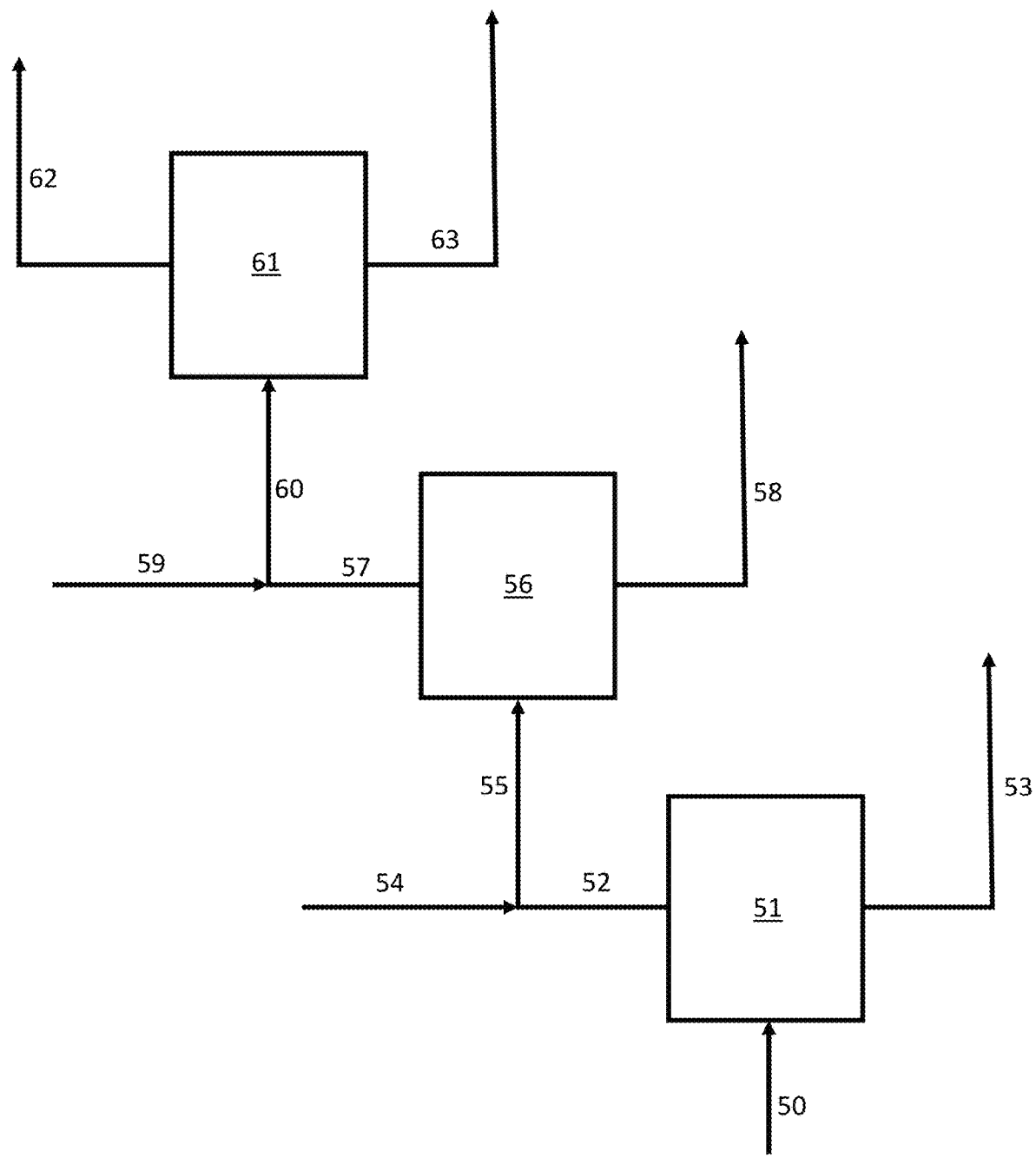
FIG. 1E is a schematic illustration showing a multi-stage separation process, according to certain embodiments.

In some embodiments, the method may be performed as a multi-step separation process. FIG. 1E is a schematic illustration showing a multi-stage separation process, according to certain embodiments. As shown in FIG. 1E, an initial mixture 50 of a first phase and a second phase (comprising a first solute and a second solute) is subjected to separation process 51. Separation process 51 can be used to produce a first liquid phase 52, which can be enriched in the first solute relative to mixture 50. Separation process 51 can also produce a second liquid phase 53, which may be enriched in the second solute relative to mixture 50.

In FIG. 1E, first liquid phase 52 can be mixed with another liquid phase 54 (which can be the same liquid that is present in liquid phase 53, or another liquid) to produce mixture 55, which can be subjected to a second separation process 56. Second separation process 56 can be used to produce phase 57, which can be further enriched in the first solute relative to mixture 55 (and, in certain embodiments, mixture 50). Second separation process 56 can also be used to produce liquid phase 58, which can be enriched in the second solute relative to mixture 55 (and, in certain embodiments, mixture 50).

In FIG. 1E, liquid phase 57 can be mixed with another liquid phase 59 (which can be the same liquid that is present in liquid phase 53 and/or liquid phase 58, or another liquid) to produce mixture 60, which can be subjected to a third separation process 61. Third separation process 61 can be used to produce phase 62, which can be further enriched in the first solute relative to mixture 60 (and, in certain embodiments, mixture 55 and/or mixture 50). Third separation process 61 can also be used to produce liquid phase 63, which can be enriched in the second solute relative to mixture 60 (and, in certain embodiments, relative to mixture 55 and/or mixture 50).

In some embodiments, the method may be performed as a continuous extraction process. The methods described herein, when used with such systems, may advantageously reduce the number of separation steps necessary to achieve efficient extraction, reduce the amount of solvent needed for the extraction, and/or allow for continuous and selective extraction of a specific cannabinoid (e.g., delta-9-tetrahydrocannabinol) from a mixture.

In some embodiments, the association of the chemical species (e.g., the delta-9-tetrahydrocannabinol and the one or more additional cannabinoids) with their respective liquid phases (e.g., the first liquid phase, the second liquid phase) in the heterogeneous liquid mixture may correlate with the ability of the chemical species to selectively partition into the different liquid phases and the volumetric ratio between the different liquid phases. For example, in a biphasic heterogeneous liquid mixture comprising a first liquid phase and a second liquid phase, the association of a chemical species with the liquid phases may correlate with an extraction factor Y. For example, for chemical species i, the extraction factor $Y_i$ may be expressed as: $Y_i = K_i \cdot (V_{1st\ liquid\ phase}/V_{2nd\ liquid\ phase})$, which is the product of the partition coefficient $K_i$ for species i and a ratio of a volume factor of the first liquid phase ($V_{1st\ liquid\ phase}$) and a volume factor of the second liquid phase ($V_{2nd\ liquid\ phase}$). In cases where the separation process is a batch separation process, the volume factor of each phase is the volume of that phase that is present (i.e., in a batch separation process, $V_{1st\ liquid\ phase}$ corresponds to the volume of the first liquid phase that is present, and $V_{2nd\ liquid\ phase}$ corresponds to the volume of the second liquid phase that is present). In cases where the separation process is one in which the first and second phases are flowed (e.g., in a continuous separation process), the volume factor of each phase is the volumetric flow rate of that phase (i.e., in a separation process in which the phases are flowing, $V_{1st\ liquid\ phase}$ corresponds to the volumetric flow rate of the first liquid phase, and $V_{2nd\ liquid\ phase}$ corresponds to the volumetric flow rate of the second liquid phase). As noted elsewhere herein, for chemical species i, the partition coefficient $K_i$ may be expressed as: $K_i = C_{i\ (1st\ liquid\ phase)}/C_{i\ (2nd\ liquid\ phase)}$, which is a ratio of the concentration of chemical species i in the first liquid phase ($C_{i,\ 1st\ liquid\ phase}$) to the concentration of chemical species i in the second liquid phase ($C_{i,\ 2st\ liquid\ phase}$).

In the context of the present disclosure, chemical species i may refer to delta-9-tetrahydrocannabinol or any of the one or more additional cannabinoids. For example, in embodiments in which the mixture comprises the delta-9-tetrahydrocannabinol and the one or more additional cannabinoids, the delta-9-tetrahydrocannabinol may have an extraction factor $Y_{d9,THC}$, which, as described above, is expressed as a product of the partition coefficient $K_{d9,THC}$ of the delta-9-tetrahydrocannabinol and the volume factor ratio ($V_{1st\ liquid\ phase}/V_{2nd\ liquid\ phase}$) between the first liquid phase and the second liquid phase, where $K_{d9,THC}$ is expressed as a ratio of the concentration of delta-9-tetrahydrocannabinol in the first liquid phase to the concentration of delta-9-tetrahydrocannabinol in the second liquid phase (e.g., $K_{d9,\ THC} = C_{d9,\ THC\ (1st\ liquid\ phase)}/C_{d9,\ THC(2nd\ liquid\ phase)}$). Similarly, each of the one or more additional cannabinoids may individually have and/or collectively have an extraction factor $Y_{cnbd,\ i}$, which, as described above, is expressed as a product of the partition coefficient $K_{cnbd,\ i}$, of the one or more additional cannabinoids and the volume factor ratio ($V_{1st\ liquid\ phase}/V_{2nd\ liquid\ phase}$) between the first liquid phase and the second liquid phase, where $K_{cnbd,\ i}$ is expressed as a ratio of the concentration of the one or more additional cannabinoids in the first liquid phase to the concentration of the one or more additional cannabinoids in the second liquid phase (e.g., $K_{cnbd,\ i} = C_{cnbd,\ i\ (1st\ liquid\ phase)}/C_{cnbd,\ i\ (2nd\ liquid\ phase)}$). For example, in embodiments in which the one or more additional cannabinoids comprise delta-8-tetrahydrocannabinol, an extraction factor $Y_{d8,\ THC}$ for the delta-8-tetrahydrocannabinol may be expressed as a product of the partition coefficient $K_{d8,THC}$ of the delta-8-tetrahydrocannabinol and the volume factor ratio ($V_{1st\ liquid\ phase}/V_{2nd\ liquid\ phase}$) between the first liquid phase and the second liquid phase, where $K_{d8,THC}$ is expressed as a ratio of the concentration of delta-8-tetrahydrocannabinol in the first liquid phase to the concentration of delta-8-tetrahydrocannabinol in the second liquid phase (e.g., $K_{d8,\ THC} = C_{d8,\ THC\ (1st\ liquid\ phase)}/C_{d8,\ THC\ (2nd\ liquid\ phase)}$). As another example, in embodiments in which the one or more additional cannabinoids comprise cannabidiol, an extraction factor $Y_{CBD}$ for the cannabidiol may be expressed as a product of the partition coefficient $K_{CBD}$ of the cannabidiol and the volumetric ratio ($V_{1st\ liquid\ phase}/V_{2nd\ liquid\ phase}$) between the first liquid phase and the second liquid phase, where $K_{CBD}$ is expressed as a ratio of the concentration of cannabidiol in the first liquid phase to the concentration of cannabidiol in the second liquid phase (e.g., $K_{CBD} = C_{CBD\ (1st\ liquid\ phase)}/C_{CBD\ (2nd\ liquid\ phase)}$).

In some embodiments, it may be advantageous to select a heterogeneous liquid mixture having a particular combination of extraction factors (e.g., $Y_{d9,THC}$, $Y_{cnbd,i}$), e.g., such as an extraction factor $Y_{d9,THC}$ of the delta-9-tetrahydrocannabinol of greater than 1 and an extraction factor $Y_{cnbd,i}$ (e.g., $Y_{d8,THC}$, $Y_{CBD}$, etc.) of the one or more additional cannabinoids of less than 1, or vice versa. Without wishing to be bound by any particular theory, it is hypothesized that such a particular combination of extraction factors may lead to efficient separation of one or more chemical species, e.g., such as the separation of delta-9-tetrahydrocannabinol from the one or more additional cannabinoids. For example, in some embodiments, the delta-9-tetrahydrocannabinol may have an extraction factor $Y_{d9,THC}$ of greater than 1, greater than or equal to 1.05, greater than or equal to 1.1, greater than or equal to 1.15, greater than or equal to 1.2, greater than or equal to 1.25, greater than or equal to 1.3, greater than or equal to 1.4, greater than or equal to 1.6, greater than or equal to 1.8, greater than or equal to 2, or greater (and/or, in some embodiments, up to 2.5, up to 3, up to 4, up to 5, up to 6, up to 8, or up to 10, or more). Combinations of the above-referenced ranges are possible (e.g., greater than 1 and up to 10). Other ranges are also possible. Additionally, in some embodiments, the one or more additional cannabinoids (e.g., delta-8-tetrahydrocannabinol, cannabidiol, etc.) may have an extraction factor $Y_{cnbd,i}$ (e.g., $Y_{d8,THC}$, $Y_{CBD}$) of less than 1, less than or equal to 0.99, less than or equal to 0.97, less than or equal to 0.95, less than or equal to 0.9, less than or equal to 0.85, less than or equal to 0.8, less than or equal to 0.7, less than or equal to 0.6, less than or equal to 0.4, less than or equal to 0.2, less than or equal to 0.1, or less (and/or down to 0.01, down to 0.001, or less). Combinations of the above-referenced ranges are possible (e.g., less than 1 and down to 0.001). Other ranges are also possible.

In embodiments in which a multi-stage liquid-liquid extraction system is employed for separating the delta-9-tetrahydrocannabinol from the one or more additional cannabinoids, the delta-9-tetrahydrocannabinol and the one or more additional cannabinoids in one or more of the plurality of stages in the extraction system may each have an extraction factor in one or more of ranges described above.

The method for separating the delta-9-tetrahydrocannabinol from the one or more additional cannabinoids may be performed at any of a variety of operating conditions. In some embodiments, the method may be performed at an operating pressure of at least 0.6 atmospheres absolute, at least 0.8 atmospheres absolute, at least 0.9 atmospheres absolute, at least 0.95 atmospheres absolute, at least 0.98 atmospheres absolute and/or less than or equal to 2.0 atmospheres absolute, less than or equal to 1.5 atmospheres absolute, less than or equal to 1.3 atmospheres absolute, less than or equal to 1.2 atmospheres absolute, less than or equal to 1.1 atmospheres absolute, less than or equal to 1.05 atmospheres absolute, and/or less than or equal to 1.02 atmospheres absolute. Combinations of the above-reference ranges are possible (e.g., at least 0.6 atmospheres absolute and less than or equal to 2.0 atmospheres absolute). Other ranges are also possible.

In some embodiments, the method may be performed at an operating temperature of greater than or equal to 5° C., greater than or equal to 10° C., greater than or equal to 15° C., greater than or equal to 20° C., greater than or equal to 30° C., greater than or equal to 40° C., or greater than or equal to 50° C. In some embodiments, the method may be performed at an operating temperature of less than or equal to 60° C., less than or equal to 50° C., less than or equal to 40° C., less than or equal to 30° C., less than or equal to 20° C., less than or equal to 15° C., or less than or equal to 10° C. Combinations of the above-referenced ranges are possible (e.g., greater than or equal to 5° C. and less than or equal to 60° C.). Other ranges are also possible.

In some embodiments, the method described herein may be employed to separate delta-9-tetrahydrocannabinol from delta-8-tetrahydrocannabinol in a mixture. In some embodiments, to separate the delta-9-tetrahydrocannabinol from the delta-8-tetrahydrocannabinol in the mixture, the mixture may be first exposed to the heterogeneous liquid mixture, e.g., as shown in FIG. 1A. The heterogeneous liquid mixture may comprise any type of first liquid phase and second liquid phase described herein. Upon exposing the mixture comprising delta-9-tetrahydrocannabinol and delta-8-tetrahydrocannabinol to the heterogeneous liquid mixture, the delta-9-tetrahydrocannabinol may preferentially associate with the first liquid phase and the delta-8-tetrahydrocannabinol may preferentially associate with the second liquid phase, e.g., as shown in FIGS. 1B-1C. In some embodiments, the heterogeneous liquid mixture may be selected based on the partition coefficients of the delta-9-tetrahydrocannabinol and the delta-8-tetrahydrocannabinol. The delta-9-tetrahydrocannabinol may have a partition coefficient $K_{d9,THC}$ in one or more ranges described elsewhere herein. Similarly, the delta-8-tetrahydrocannabinol may have a partition coefficient $K_{d8,THC}$ in one or more ranges described above with respect to the partition coefficient $K_{cnbd,i}$ of the one or more additional cannabinoids. In some cases, the delta-9-tetrahydrocannabinol and the delta-8-tetrahydrocannabinol may have a ratio of $K_{d9,THC}$ to $K_{d8,THC}$ in one or more of the ranges described above with respect to $K_{d9,THC}$ to $K_{cnbd,i}$.

In some embodiments, the method described herein may be employed to separate delta-9-tetrahydrocannabinol from cannabidiol in a mixture. In some embodiments, to separate the delta-9-tetrahydrocannabinol from the cannabidiol in the mixture, the mixture may be first exposed to the heterogeneous liquid mixture, e.g., as shown in FIG. 1A. The heterogeneous liquid mixture may comprise any type of first liquid phase and second liquid phase described herein. Upon exposing the mixture comprising delta-9-tetrahydrocannabinol and cannabidiol to the heterogeneous liquid mixture, the delta-9-tetrahydrocannabinol may preferentially associate with the first liquid phase and the cannabidiol may preferentially associate with the second liquid phase, e.g., as shown in FIGS. 1B-1C. In some embodiments, the heterogeneous liquid mixture may be selected based on the partition coefficients of the delta-9-tetrahydrocannabinol and the cannabidiol. The delta-9-tetrahydrocannabinol may have a partition coefficient $K_{d9,THC}$ in one or more ranges described elsewhere herein. The cannabidiol may have a partition coefficient $K_{CBD}$ in one or more ranges described above with respect to the partition coefficient $K_{cnbd,i}$ of the one or more additional cannabinoids. In some cases, the delta-9-tetrahydrocannabinol and the cannabidiol may have a ratio of $K_{d9,THC}$ to $K_{CBD}$ in one or more of the ranges described above with respect to $K_{d9,THC}$ to $K_{cnbd,i}$.

Certain embodiments related to an ingestible composition. In one set of embodiments, the ingestible composition comprises delta-9-tetrahydrocannabinol and, optionally, one or more additional cannabinoids. The one or more additional cannabinoids may include any of a variety of additional cannabinoids described elsewhere herein. For example, the one or more additional cannabinoids may comprise delta-8-tetrahydrocannabinol. Alternatively or additionally, the one or more additional cannabinoids may comprise cannabidiol.

The ingestible composition may have any of a variety of appropriate volumes. In some embodiments, the ingestible composition may have a volume of at least 1 mm³ (e.g., at least 2 mm³, at least 5 mm³, at least 7 mm³, or at least 2 mm³). In some embodiments, the ingestible composition may have a volume of up to 20 mm³ (e.g., up to 40 mm³, up to 60 mm³, up to least 80 mm³, or up to 100 mm³). Combinations of the above-referenced ranges are possible (e.g., at least 2 mm³ and up to 100 mm³). Other ranges are also possible.

The ingestible composition may comprise the delta-9-tetrahydrocannabinol in any of a variety of appropriate amounts. In some embodiments, the amount of delta-9-tetrahydrocannabinol within the composition may be at least 0.01 wt %, at least 0.1 wt %, at least 1 wt %, at least 10 wt %, at least 20 wt %, at least 50 wt %, at least 75 wt %, at least 90 wt %, or more. In some embodiments, the amount of delta-9-tetrahydrocannabinol within the composition may be up to 2000 mg, up to 2500 mg, up to 3000 mg, up to 4000 mg, or more. Combinations of the above-referenced ranges are also possible (e.g., at least 0.01 mg and up to 4000 mg). Other ranges are also possible.

The delta-9-tetrahydrocannabinol and the one or more additional cannabinoids (e.g., delta-8-tetrahydrocannabinol, cannabidiol, etc.) may be present in the composition in any appropriate molar ratio. For example, a molar ratio of the delta-9-tetrahydrocannabinol to the one or more cannabinoids within the ingestible composition may be greater than or equal to 3:1 (e.g., greater than or equal to 5:1, greater than or equal to 9:1, greater than or equal to 95:5, greater than or equal to 97:3, greater than or equal to 99:1, or greater than or equal to 99.9:0.1).

When a range of values ("range") is listed, it encompasses each value and sub-range within the range. A range is inclusive of the values at the two ends of the range unless otherwise provided. For example "$C_{1-6}$ alkyl" encompasses, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("heteroC$_{1-20}$ alkyl"). In certain embodiments, a heteroalkyl group refers to a saturated group having from 1 to 12 carbon atoms and 1 or more heteroatoms within the parent chain ("heteroC$_{1-12}$ alkyl"). In some embodiments, a heteroalkyl group is a saturated group having 1 to 11 carbon atoms and 1 or more heteroatoms within the parent chain ("heteroC$_{1-11}$ alkyl"). In some embodiments, a heteroalkyl group is a saturated group having 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-12}$ alkyl. In certain embodiments, the heteroalkyl group is a substituted heteroC$_{1-12}$ alkyl.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C=C double bond for which the stereochemistry is not specified (e.g.,

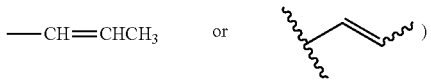

) may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 1 to 20 carbon atoms, at least one double bond, and 1 or more heteroatoms within the parent chain ("heteroC$_{1-20}$ alkenyl"). In certain embodiments, a heteroalkenyl group refers to a group having from 1 to 12 carbon atoms, at least one double bond, and 1 or more heteroatoms within the parent chain ("heteroC$_{1-12}$ alkenyl"). In certain embodiments, a heteroalkenyl group refers to a group having from 1 to 11 carbon atoms, at least one double bond, and 1 or more heteroatoms within the parent chain ("heteroC$_{1-11}$ alkenyl"). In certain embodiments, a heteroalkenyl group refers to a group having from 1 to 10 carbon atoms, at least one double bond, and 1 or more heteroatoms within the parent chain ("heteroC$_{1-10}$ alkenyl"). In some embodiments, a heteroalkenyl group has 1 to 9 carbon atoms at least one double bond, and 1 or more heteroatoms within the parent chain ("heteroC$_{1-9}$ alkenyl"). In some embodiments, a heteroalkenyl group has 1 to 8 carbon atoms, at least one double bond, and 1 or more heteroatoms within the parent chain ("heteroC$_{1-8}$ alkenyl"). In some embodiments, a heteroalkenyl group has 1 to 7 carbon atoms, at least one double bond, and 1 or more heteroatoms within the parent chain ("heteroC$_{1-7}$ alkenyl"). In some embodiments, a heteroalkenyl group has 1 to 6 carbon atoms, at least one double bond, and 1 or more heteroatoms within the parent chain ("heteroC$_{1-6}$ alkenyl"). In some embodiments, a heteroalkenyl group has 1 to 5 carbon atoms, at least one double bond, and 1 or 2 heteroatoms within the parent chain ("heteroC$_{1-5}$ alkenyl"). In some embodiments, a heteroalkenyl group has 1 to 4 carbon atoms, at least one double bond, and 1 or 2 heteroatoms within the parent chain ("heteroC$_{1-4}$ alkenyl"). In some embodiments, a heteroalkenyl group has 1 to 3 carbon atoms, at least one double bond, and 1 heteroatom within the parent chain ("heteroC$_{1-3}$ alkenyl"). In some embodiments, a heteroalkenyl group has 1 to 2 carbon atoms, at least one double bond, and 1 heteroatom within the parent chain ("heteroC$_{1-2}$ alkenyl"). In some embodiments, a heteroalkenyl group has 1 to 6 carbon atoms, at least one double bond, and 1 or 2 heteroatoms within the parent chain ("heteroC$_{1-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{1-20}$ alkenyl. In certain embodiments, the heteroalkenyl group is a substituted heteroC$_{1-20}$ alkenyl.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_{1-20}$ alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("heteroC$_{1-20}$ alkynyl"). In certain embodiments, a heteroalkynyl group refers to a group having from 1 to 10 carbon atoms, at least one triple bond, and 1 or more heteroatoms within the parent chain ("heteroC$_{1-10}$ alkynyl"). In some embodiments, a heteroalkynyl group has 1 to 9 carbon atoms, at least one triple bond, and 1 or more heteroatoms within the parent chain ("heteroC$_{1-9}$ alkynyl"). In some embodiments, a heteroalkynyl group has 1 to 8 carbon atoms, at least one triple bond, and 1 or more heteroatoms within the parent chain ("heteroC$_{1-8}$ alkynyl"). In some embodiments, a heteroalkynyl group has 1 to 7 carbon atoms, at least one triple bond, and 1 or more heteroatoms within the parent chain ("heteroC$_{1-7}$ alkynyl"). In some embodiments, a heteroalkynyl group has 1 to 6 carbon atoms, at least one triple bond, and 1 or more heteroatoms within the parent chain ("heteroC$_{1-6}$ alkynyl"). In some embodiments, a heteroalkynyl group has 1 to 5 carbon atoms, at least one triple bond, and 1 or 2 heteroatoms within the parent chain ("heteroC$_{1-5}$ alkynyl"). In some embodiments, a heteroalkynyl group has 1 to 4 carbon atoms, at least one triple bond, and 1 or 2 heteroatoms within the parent chain ("heteroC$_{1-4}$ alkynyl"). In some embodiments, a heteroalkynyl group has 1 to 3 carbon atoms, at least one triple bond, and 1 heteroatom within the parent chain ("heteroC$_{1-3}$ alkynyl"). In some embodiments, a heteroalkynyl group has 1 to 2 carbon atoms, at least one triple bond, and 1 heteroatom within the parent chain ("heteroC$_{1-2}$ alkynyl"). In some embodiments, a heteroalkynyl group has 1 to 6 carbon atoms, at least one triple bond, and 1 or 2 heteroatoms within the parent chain ("heteroC$_{1-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{1-20}$ alkynyl. In certain embodiments, the heteroalkynyl group is a substituted heteroC$_{1-20}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 14 ring carbon atoms ("C$_{3-14}$ carbocyclyl"). In some embodiments, a carbocyclyl group has 3 to 13 ring carbon atoms ("C$_{3-13}$ carbocyclyl"). In some embodiments, a carbocyclyl group has 3 to 12 ring carbon atoms ("C$_{3-12}$ carbocyclyl"). In some embodiments, a carbocyclyl group has 3 to 11 ring carbon atoms ("C$_{3-11}$ carbocyclyl"). In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1] heptanyl (C$_7$), bicyclo[2.2.2]octanyl (C$_8$), and the like. Exemplary C$_{3-10}$ carbocyclyl groups include the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. Exemplary C$_{3-8}$ carbocyclyl groups include the aforementioned C$_{3-10}$ carbocyclyl groups as well as cycloundecyl (C$_{11}$), spiro[5.5]undecanyl (C$_{11}$), cyclododecyl (C$_{12}$), cyclododecenyl (C$_{12}$), cyclotridecane (C$_{13}$), cyclotetradecane (C$_{14}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "unsaturated" or "partially unsaturated" refers to a moiety that includes at least one double or triple bond.

The term "saturated" or "fully saturated" refers to a moiety that does not contain a double or triple bond, e.g., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which is substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The following examples are intended to illustrate certain embodiments of the present invention, but do not exemplify the full scope of the invention.

Examples 1-9

These examples describe the separation of delta-9-tetrahydrocannabinol from delta-8-tetrahydrocannabinol using various types of liquid mixtures, in accordance with certain embodiments.

A cannabinoid sample rich in overall tetrahydrocannabinol (THC) content (e.g., ~90% THC) with a low cannabidiol (CBD) content was exposed to various liquid mixtures in Examples 1-9. The cannabinoid sample contained both delta-9-tetrahydrocannabinol with delta-8-tetrahydrocannabinol. The liquid mixtures included an organic phase as the first liquid phase and a water soluble phase as the second liquid phase. The organic phase and the water soluble phase were in 1:1 volume ratio for all analyses. Various hydrocarbons were evaluated as the organic phase. These hydrocarbons included hexane, heptane, cyclohexane, pentane, 1-hexene, toluene, benzene, 1-octadecene, and dodecane. Various amide based solvents were evaluated as the water soluble phase. These amide based solvents included formamide (F), dimethyl formamide (DMF), methyl formamide (MF), dibutyl formamide (DBF).

Example 1. A mixture containing formamide (F) and dimethyl formamide (DMF) at a volume ratio of 9:16 (36% F and 64% DMF) was used as the water soluble phase. Hexane was used as the organic phase.

Example 2. A mixture containing formamide (F) and dimethyl formamide (DMF) at a volume ratio of 9:16 (36% F and 64% DMF) was used as the water soluble phase. Heptane was used as the organic phase.

Example 3. A mixture containing formamide (F) and dimethyl formamide (DMF) at a volume ratio of 9:16 (36% F and 64% DMF) was used as the water soluble phase. Cyclohexane was used as the organic phase.

Example 4. A mixture containing formamide (F) and dimethyl formamide (DMF) at a volume ratio of 9:16 (36% F and 64% DMF) was used as the water soluble phase. Pentane was used as the organic phase.

Example 5. A mixture containing formamide (F) and dimethyl formamide (DMF) at a volume ratio of 9:16 (36% F and 64% DMF) was used as the water soluble phase. 1-Hexene was used as the organic phase.

Example 6. A mixture containing formamide (F) and dimethyl formamide (DMF) at a volume ratio of 1:1 (50% F and 50% DMF) was used as the water soluble phase. Dodecane was used as the organic phase.

Example 7. A mixture of formamide (F) and methyl formamide (MF) at a volume ratio of 1:1 (50% F and 50% MF) was used as the water soluble phase. Hexane was used as the organic phase.

Example 8. A mixture of formamide (F) and methyl formamide (MF) at a volume ratio of 2:3 (40% F and 60% MF) was used as the water soluble phase. Hexane was used as the organic phase.

Example 9. A mixture of formamide (F) and dimethyl formamide (DMF) and dibutyl formamide (DBF) at a volume ratio of 1:3:1 (20% F and 60% DMF and 20% DBF) was used as the water soluble phase. Hexane was used as the organic phase.

Table 1 shows the partition coefficients, $K_{d9,\ THC}$ for delta-9-tetrahydrocannabinol and $K_{d8,\ THC}$ for delta-8-tetrahydrocannabinol, in each liquid mixture. The partition coefficients for each component (e.g., delta-9-tetrahydrocannabinol, delta-8-tetrahydrocannabinol) in the liquid mixture were determined by calculating a ratio of the concentration of the component in the water soluble phase over concentration of the component in the organic phase.

TABLE 1

Partition coefficients for each liquid mixture.

| | Water soluble phase | Organic Phase | $K_{d9,\ THC}$ | $K_{d8,\ THC}$ | $K_{d9,\ THC}/K_{d8,\ THC}$ |
|---|---|---|---|---|---|
| Example 1 | F:DMF (9:16) | Hexane | 1.27 | 0.86 | 1.47 |
| Example 2 | F:DMF (9:16) | Heptane | 1.61 | 1.11 | 1.45 |
| Example 3 | F:DMF (9:16) | Cyclohexane | 0.57 | 0.39 | 1.48 |
| Example 4 | F:DMF (9:16) | Pentane | 1.54 | 1.13 | 1.36 |
| Example 5 | F:DMF (9:16) | 1-Hexene | 0.53 | 0.39 | 1.37 |
| Example 6 | F:DMF (1:1) | Dodecane | 1.08 | 0.78 | 1.39 |
| Example 7 | F:MF (1:1) | Hexane | 0.52 | 0.44 | 1.20 |
| Example 8 | F:MF (2:3) | Hexane | 1.41 | 1.15 | 1.23 |
| Example 9 | F:DMF:DBF (1:3:1) | Hexane | 1.04 | 0.75 | 1.39 |

The cannabinoid sample was exposed to various liquid mixtures in Examples 1-9. The liquid mixtures in Examples 1-6 and 9 exhibited efficient separation of the delta-9-tetrahydrocannabinol and delta-8-tetrahydrocannabinol. The liquid mixtures in Examples 7-8 also demonstrated separation of the delta-9-tetrahydrocannabinol and delta-8-tetrahydrocannabinol, but the separation was less efficient than those observed Examples 1-6 and 9. As shown in Example 9, efficient separation can be obtained using a water soluble phase containing several amide-containing liquids (e.g., such as three amide-containing liquids).

As shown in Table 1, a liquid mixture that can be employed to achieve efficient separation may be associated with a certain set of properties. In general, the liquid mixtures were substantially immiscible such that two distinct phases were established.

Furthermore, it was observed that a liquid mixture having relatively high partition coefficient ratio of $K_{d9,\ THC}$ to $K_{d8,\ THC}$ (e.g., at least about 1.3) led to especially efficient separation, as shown in Examples 1-6 and 9. The partition coefficient ratio may be used as an indication of whether a liquid mixture can be used for efficient separation of components in a mixture. For example, a relatively high partition ratio indicates a higher selectivity for delta-9-tetrahydrocannabinol relative to delta-8-tetrahydrocannabinol, and thereby a more efficient separation. A liquid mixture having a relatively low partition coefficient ratio may be less efficient as it may require a more solvent consumption and/or a larger number of extraction stages for separation of the delta-9-tetrahydrocannabinol from the delta-8-tetrahydrocannabinol.

Additionally or alternatively, a liquid mixture that can be used for efficient separation can have a $K_{d9,\ THC}$ of above 1 and a $K_{d8,\ THC}$ of below 1. In some cases, it may be advantageous to use liquid mixtures that have the ability (or can be adjusted to have a composition) to result in a $K_{d9,\ THC}$ of above 1 and a $K_{d8,\ THC}$ of below 1. As an example, for a water soluble phase comprising formamide (F) and dimethyl formamide (DMF), the relative amounts of F to DMF can be adjusted to result in a $K_{d9, THC}$ of above 1 and a $K_{d8, THC}$ of below 1.

The liquid mixtures in Examples 1-6 and 9 may be employed for particularly efficient separation because the liquid mixtures had a relatively high partition coefficient ratio (e.g., at least 1.3), comprised 2 immiscible phases, and could be adjusted to have a $K_{d9, THC}$ of above 1 and a $K_{d8, THC}$ of below 1. The liquid mixtures in Examples 7-8, although less efficient than those in Examples 1-6 (e.g., having a lower partition coefficient ratio), also comprised 2 immiscible phases and may also be employed for separation of delta-9-tetrahydrocannabinol from delta-8-tetrahydrocannabinol.

Example 10

This example describes the separation of delta-9-tetrahydrocannabinol from cannabinol using a heterogeneous liquid mixture, in accordance with certain embodiments.

A cannabinoid sample rich in cannabidiol (CBD) content (~90% CBD) relative to tetrahydrocannabinol (THC) content was exposed a liquid mixture. The cannabinoid sample comprised delta-9-tetrahydrocannabinol. The liquid mixtures included an organic phase and a water soluble phase. The organic phase and the water soluble phase were in 1:1 volume ratio for all analyses. A mixture containing formamide (F) and dimethyl formamide (DMF) at a volume ratio of 65% F to 35% DMF was used as the water soluble phase. Hexane was used as the organic phase. The partition coefficient for each component (e.g., delta-9-tetrahydrocannabinol, cannabidiol) in the liquid mixture was determined by calculating a ratio of the concentration of the component in the water soluble phase over concentration of the component in the organic phase. While cannabidiol had a partition coefficient $K_{CBD}$ of 1.87, delta-9-tetrahydrocannabinol had a partition coefficient $K_{d9, THC}$ of 0.4. The liquid mixture resulted in efficient separation of delta-9-tetrahydrocannabinol from cannabidiol.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Some embodiments may be embodied as a method, of which various examples have been described. The acts performed as part of the methods may be ordered in any suitable way. Accordingly, embodiments may be constructed in which acts are performed in an order different than illustrated, which may include different (e.g., more or less) acts than those that are described, and/or that may involve performing some acts simultaneously, even though the acts are shown as being performed sequentially in the embodiments specifically described above.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for separating delta-9-tetrahydrocannabinol from delta-8-tetrahydrocannabinol, comprising:
   exposing a mixture comprising the delta-9-tetrahydrocannabinol and the delta-8-tetrahydrocannabinol to a heterogeneous liquid mixture, wherein the heterogeneous liquid mixture comprises a first liquid phase and a second liquid phase,
   wherein:
      the mole fraction of the delta-9-tetrahydrocannabinol relative to the sum of the delta-9-tetrahydrocannabinol and the delta-8-tetrahydrocannabinol in the first liquid phase is greater than the mole fraction of the delta-9-tetrahydrocannabinol relative to the sum of the delta-9-tetrahydrocannabinol and the delta-8-tetrahydrocannabinol in the mixture; and
      the mole fraction of the delta-8-tetrahydrocannabinol relative to the sum of the delta-8-tetrahydrocannabinol and the delta-9-tetrahydrocannabinol in the second liquid phase is greater than the mole fraction of the delta-8-tetrahydrocannabinol relative to the sum of the delta-8-tetrahydrocannabinol and the delta-9-tetrahydrocannabinol in the mixture.

2. The method of claim 1, wherein the delta-9-tetrahydrocannabinol preferentially associates with the first liquid phase.

3. The method of claim 2, wherein the delta-8-tetrahydrocannabinol preferentially associates with the second liquid phase.

4. The method of claim 1, wherein the delta-9-tetrahydrocannabinol comprises one or more stereoisomers of delta-9-tetrahydrocannabinol.

5. The method of claim 4, wherein the delta-9-tetrahydrocannabinol comprises (−)-delta-9-trans-tetrahydrocannabinol, (+)-delta-9-trans-tetrahydrocannabinol, (−)-delta-9-cis-tetrahydrocannabinol, and/or (+)-delta-9-cis-tetrahydrocannabinol.

6. The method of claim 1, wherein the delta-9-tetrahydrocannabinol has a partition coefficient $K_{d9,THC}$ between the first liquid phase and the second liquid phase, wherein the delta-8-tetrahydrocannabinol has a partition coefficient $K_{d8,THC}$ between the first liquid phase and the second liquid phase, and wherein a ratio of $K_{d9,THC}$ to $K_{d8,THC}$ is greater than or equal to 1.3.

7. The method of claim 1, wherein the delta-9-tetrahydrocannabinol has a partition coefficient $K_{d9,THC}$ between the first liquid phase and the second liquid phase of greater than 1.

8. The method of claim 7, wherein the delta-8-tetrahydrocannabinol has a partition coefficient $K_{d8,THC}$ between the first liquid phase and the second liquid phase of less than 1.

9. The method of claim 1, wherein the extraction factor of the delta-9-tetrahydrocannabinol ($Y_{d9,THC}$) is greater than 1.

10. The method of claim 9, wherein the extraction factor of the delta-8-tetrahydrocannabinol ($Y_{d8,THC}$) is less than 1.

11. The method of claim 1, wherein the first liquid phase comprises at least one liquid comprising an amide group.

12. The method of claim 1, wherein the first liquid phase comprises at least two liquids, wherein each of the two liquids comprises an amide group.

13. The method of claim 1, wherein the first liquid phase comprises formamide, acetamide, propanamide, butanamide, dimethyl formamide, diethyl formamide, methyl formamide, dimethyl acetamide, diethyl acetamide, dimethyl propanamide, diethyl propanamide, dimethyl butanamide, and/or diethyl butanamide.

14. The method of claim 1, wherein the first liquid phase comprises a mixture of formamide and dimethylformamide.

15. The method of claim 14, wherein a mass ratio of formamide to dimethylformamide in the mixture is from 20:80 to 80:20.

16. The method of claim 1, wherein the second liquid phase comprises a $C_3$ to $C_{20}$ aliphatic hydrocarbon.

17. The method of claim 16, wherein the aliphatic hydrocarbon is unsubstituted.

18. The method of claim 16, wherein the aliphatic hydrocarbon comprises an alkyl, an alkenyl, an alkynyl, a cycloalkyl, a cycloalkenyl, and/or a cycloalkynyl group.

19. The method of claim 16, wherein the aliphatic hydrocarbon comprises pentane, pentene, pentyne, cyclopentane, cyclopentene, cyclopentyne, hexane, hexene, hexyne, cyclohexane, cyclohexene, cyclohexyne, heptane, heptene, heptyne, cycloheptane, cycloheptene, cycloheptyne, dodecane, dodecene, dodecyne, cyclododecane, cyclododecene, and/or cyclododecyne.

20. The method of claim 1, wherein a mass ratio of the first liquid phase to the second liquid phase is from 95:5 to 5:95.

21. The method of claim 1, wherein the mixture further comprises one or more cannabinoids different from delta-9-tetrahydrocannabinol and delta-8-tetrahydrocannabinol.

22. The method of claim 1, wherein the method has a delta-9-tetrahydrocannabinol extraction efficiency of greater than or equal to 80%.

23. A method for separating delta-9-tetrahydrocannabinol from one or more additional cannabinoids, comprising:
   exposing a mixture comprising the delta-9-tetrahydrocannabinol and the one or more additional cannabinoids to a heterogeneous liquid mixture, wherein the heterogeneous liquid mixture comprises a first liquid phase and a second liquid phase,
   wherein:
      the mole fraction of the delta-9-tetrahydrocannabinol relative to the sum of the delta-9-tetrahydrocannabinol and the one or more additional cannabinoids in the first liquid phase is greater than the mole fraction of the delta-9-tetrahydrocannabinol relative to the sum of the delta-9-tetrahydrocannabinol and the one or more additional cannabinoids in the mixture; and
      the mole fraction of the one or more additional cannabinoids relative to the sum of the one or more additional cannabinoids and the delta-9-tetrahydrocannabinol in the second liquid phase is greater than the mole fraction of the one or more additional cannabinoids relative to the sum of the one or more additional cannabinoids and the delta-9-tetrahydrocannabinol in the mixture.

24. The method of claim 23, wherein the delta-9-tetrahydrocannabinol preferentially associates with the first liquid phase.

25. The method of claim 24, wherein the one or more additional cannabinoids preferentially associates with the second liquid phase.

26. The method of claim 23, wherein the one or more cannabinoids comprises cannabidiol.

27. The method of claim 23, wherein the delta-9-tetrahydrocannabinol has a partition coefficient $K_{d9,THC}$ between the first liquid phase and the second liquid phase, wherein the one or more additional cannabinoids have a partition coefficient $K_{cnbd}$ between the first liquid phase and the second liquid phase, and wherein a ratio of $K_{d9,THC}$ to $K_{cnbd}$ is greater than or equal to 1.3.

28. The method of claim 23, wherein the delta-9-tetrahydrocannabinol has a partition coefficient $K_{d9,THC}$ between the first liquid phase and the second liquid phase of greater than 1.

29. The method of claim 28, wherein the one or more cannabinoids has a partition coefficient $K_{cnbd}$ between the first liquid phase and the second liquid phase of less than 1.

30. The method of claim 23, wherein the extraction factor of the delta-9-tetrahydrocannabinol ($Y_{d9,THC}$) is greater than 1.

* * * * *